United States Patent
Kasarle et al.

(10) Patent No.: US 11,202,821 B2
(45) Date of Patent: Dec. 21, 2021

(54) GLUCOSE OXIDASE COMPOSITIONS

(71) Applicant: VEGANUTRITECH LLP, Mumbai (IN)

(72) Inventors: Sharad Krishnaji Kasarle, Mumbai (IN); Divya Sharad Kasarle, Mumbai (IN)

(73) Assignee: VEGANUTRITECH LLP, Mumbai (IN)

( * ) Notice: Subject to any disclaimer, the term of this patent is extended or adjusted under 35 U.S.C. 154(b) by 258 days.

(21) Appl. No.: 16/324,089

(22) PCT Filed: Aug. 8, 2017

(86) PCT No.: PCT/IN2017/050332
§ 371 (c)(1),
(2) Date: Feb. 7, 2019

(87) PCT Pub. No.: WO2018/029705
PCT Pub. Date: Feb. 15, 2018

(65) Prior Publication Data
US 2019/0175703 A1 Jun. 13, 2019

(30) Foreign Application Priority Data

Aug. 9, 2016 (IN) .............................. 201621027241
Apr. 17, 2017 (WO) ................. PCT/IN2017/000084

(51) Int. Cl.
| | | |
|---|---|---|
| A23L 33/21 | (2016.01) | |
| A61K 38/44 | (2006.01) | |
| A23L 27/30 | (2016.01) | |
| A23L 29/30 | (2016.01) | |
| A23L 33/125 | (2016.01) | |
| A23L 33/195 | (2016.01) | |
| A23L 29/206 | (2016.01) | |
| A23L 33/22 | (2016.01) | |
| A23L 33/17 | (2016.01) | |
| C12N 9/04 | (2006.01) | |
| A23L 29/00 | (2016.01) | |
| A23L 9/10 | (2016.01) | |
| A61K 31/716 | (2006.01) | |
| A61K 31/733 | (2006.01) | |
| A61K 47/10 | (2017.01) | |
| A61K 47/26 | (2006.01) | |

(52) U.S. Cl.
CPC ............. A61K 38/443 (2013.01); A23L 9/10 (2016.08); A23L 27/30 (2016.08); A23L 27/31 (2016.08); A23L 27/33 (2016.08); A23L 27/34 (2016.08); A23L 27/36 (2016.08); A23L 27/37 (2016.08); A23L 29/06 (2016.08); A23L 29/206 (2016.08); A23L 29/30 (2016.08); A23L 29/37 (2016.08); A23L 33/125 (2016.08); A23L 33/17 (2016.08); A23L 33/195 (2016.08); A23L 33/21 (2016.08); A23L 33/22 (2016.08); A61K 31/716 (2013.01); A61K 31/733 (2013.01); A61K 47/10 (2013.01); A61K 47/26 (2013.01); C12N 9/0006 (2013.01); C12Y 101/03004 (2013.01); A23V 2002/00 (2013.01); A23V 2200/00 (2013.01)

(58) Field of Classification Search
CPC combination set(s) only.
See application file for complete search history.

(56) References Cited

U.S. PATENT DOCUMENTS 7,892,536 B2    2/2011   Kelemen et al.

OTHER PUBLICATIONS

Akhila JS, et al., "Effects of the insulin plant (*Costus igneus*) leaves on dexamethasone-induced hyperglycemia", Int. J Ayurveda Res., 2010, 1: 100-102.
Barman, T.E., Enzyme Handbook, 1969, p. 112-113, vol. I, Springer-Verlag Berlin Heidelberg GmbH.
Faiyaz Ahmed, et al., "In vitro hypoglycemic effects of selected dietary fiber sources", J Food Sci Technol., 2011, 48(3): 285-289.
International Search Report dated Nov. 22, 2017.
Monti Mariana, et al., "Starch and fiber intake and glucose postprandial response of doges", Cienc. Rural, 2016 vol. 46 No 2.
Written Opinion dated Nov. 22, 2017.

*Primary Examiner* — Heidi Reese
(74) *Attorney, Agent, or Firm* — Gorman IP Law, APC

(57) ABSTRACT

Glucose oxidase and further compositions are described. The glucose oxidase compositions have glucose oxidase and at least one ingredient selected from one or more of carbohydrate (e.g. dietary fibre or saccharide), polyol or sugar alcohol while further compositions are sweeteners, food, compositions for fortification of food, nutraceuticals and pharmaceuticals. The compositions incorporate low glycemic index nutritive compound of glycemic index less than 70, preferably less than 50, and are in the form of powders, granules, crystalline compositions, flours, pills, tablets, capsules, pellets, powder for oral suspensions, gels, liquid solutions and suspensions, and sterile preparations. The compositions regulate one or more diseases/conditions, including but not limited to those associated with blood, kidney, thyroid, nerves, joints, weight, diabetes, oxidative stress, cardiovascular disease, insulin resistance, amyloid foot ulcers, cataract, glaucoma, hypertension, metabolic disorders, digestive disorders, polycystic ovarian syndrome, mastopathy, dupuytren's contracture, gingivitis, periodontitis, dental caries, mouth disorders, cognitive dysfunction, and Parkinson's disease.

30 Claims, No Drawings

GLUCOSE OXIDASE COMPOSITIONS

FIELD OF THE INVENTION

This application is the National Phase Under 35 USC § 371 of PCT International Application No. PCT/IN2017/050332 filed on Aug. 8, 2017 which claims priority under 35 U.S.C. § 119 on PCT International Application No. PCT/IN2017/000084 filed on Apr. 17, 2017 and Patent Application No. 201621027241 filed in India on Aug. 9, 2016, the entire contents of each of which are hereby incorporated by reference.

The invention relates to compositions which include glucose oxidase enzyme as a primary ingredient, hereinafter referred as glucose oxidase compositions. These glucose oxidase compositions can further produce various other further compositions such as food compositions, compositions for fortification of food, sweetener compositions, nutraceutical compositions, pharmaceutical compositions etc. hereinafter referred as "further compositions".

Glucose oxidase compositions have several health benefits for healthy individuals and also individuals suffering from one or more of following:
hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's and Parkinson's disease.

Glucose oxidase compositions may have from 0.01-95% of glucose oxidase and an additional ingredient in an amount of at least 5%. Preferably the additional ingredient is a carbohydrate. Most preferably carbohydrate is a dietary fibre. Carbohydrate may also include saccharides. The dietary fibre includes one or more ingredients from dietary fibres such as one or more of non-starch polysaccharides, methylcellulose, β-glucans, mucilage, waxes, cyclodextrins, celluloses, hemicelluloses, starches, dextrins, inulins, lignins, chitins, pectins, beta-glucans (from oat bran, whole oats, oatrim or rolled oats, whole grain or dry-milled barley), fibres extracted from legumes, Chitosan, natural gums, xanthan gum, guar gum, gellan gum, tara gum, gum acacia, gum arabic, beta-mannan, locust bean gum (carob), psyllium seed husk gum, galactomannan (including fenumannans), glucomannan or konjac, karaya, tragacanth, hexoses, pentoses, resistant starch, plant waxes, alginic acids (alginates), natriumalginat, kaliumalginat, ammoniumalginat, calciumalginat, propylenglycolalginat, (PGA), agar, carrageen, raffinose, xylose, polydextrose, lactulose, vegetable gums, polysaccharide, heterosaccharides, agar-agar, alginate, oligosaccharides, arabinoxylan (a hemicellulose), fructooligosaccharides (FOS, oligofructose), galacto-oligosaccharides (GOS), human milk oligosaccharides (HMO), isomalto-oligosaccharides (IMO), lactosucrose, mannan-oligosaccharides (MOS), raffinose, stachyose, verbascose and derivatives thereof.

Glucose oxidase compositions are incorporated to prepare further sweetener, food, nutraceutical or pharmaceutical compositions prepared and they are in the form of one or more of the following:
Powder compositions, granule compositions, crystalline compositions, flour compositions, pill, tablet, hard and soft capsule compositions, pellet compositions, powder for oral suspensions, liquid solutions and suspensions and sterile preparations etc, The sweetener composition, a further composition prepared from glucose oxidase composition includes a low glycemic index nutritive ingredient wherein such compositions can be used in place of sugar or artificial/natural sweetener. A low glycemic index nutritive ingredient in such compositions contains at least one ingredient which tastes sweet and hereinafter referred as a sweetening agent. A low glycemic index nutritive ingredient selected from at least one low glycemic index compound with a glycemic index of less than 70. More particularly, the invention relates to a sweetener composition comprising Glucose oxidase (GOD) enzyme in a concentration range of 0.1%-99.99% by weight of the total composition and at least one low glycemic index nutritive ingredient including one or more of polyols and saccharides. Furthermore, the invention relates to modified sugar, an article of food, a nutraceutical composition, a pharmaceutical composition comprising the Glucose oxidase (GOD) enzyme compositions

DESCRIPTION OF THE RELATED ART

Nutraceutical sweetener compositions are widely known in the art. Several compositions have been developed for modifying the taste; appearance and mouth feel profile of consumables that contain these sweeteners. Natural caloric sugars, such as sucrose, fructose, and glucose are widely used in beverages, food and pharmaceutical industries due to their pleasant taste. While sweeteners such as sucrose impart a desirable taste, it is high on calories and exhibits a lot of disadvantages on health including obesity, cardiovascular diseases and certain serious metabolic disorders. Therefore, there was a need for alternate low-calorie sweeteners with a sugar-like taste.

The compositions available in market also contain artificial sweeteners like saccharine, Aspartame, Sucralose, Acesulfame K, Neotame, Alitame, etc. However, such low calorie sweeteners exhibit undesirable tastes such as lingering sweetness; bitter after taste for a long time after consumption, metallic taste and such other unpleasant tastes. Due to these reasons, the use of known natural sweeteners in foods or beverages, cause an unbalanced flavour profile or such foods are rendered with unpalatable sensory attributes when such sweeteners are included in their preparation. Moreover, health hazards such as neurotoxicity, renal toxicity, carcinogenicity, and such other which life threatening hazards are also known to be reported when such artificial sweeteners are included in the food compositions. These artificial sweeteners are hence regarded as non-nutritive sweeteners.

Furthermore, commercially available artificial sweeteners also suffer from poor stability profile when used in foods and beverages. The available compositions are not safe and thus are not recommended, particularly for children and pregnant women. Also, artificial sweeteners are intensely sweet, e.g. Sucralose is 600 times sweeter than sugar. The available compositions further contain bulking agents in the formulation to balance the sweetness profile. The bulking agents often used include dextrose or maltodextrin which have a Glycemic Index which is higher than that of sugar. The glycemic index of Dextrose is 100, that of maltodextrin is 110 and whereas the glycemic index of sugar is 65. These bulking agents would be absorbed in vivo which is contrary to the purpose of the use of the non-sugar sweeteners. Thus, the inclusion of these bulking agents in the sweetener composition would actually cause more harm to the body than sugar.

Hence there is a need to develop a sweetener composition having sugar-like characteristics in terms of taste, wherein the sweetener composition is again low on calories and also has a low glycemic index. Further, there is need to develop a sweetener composition which is free from high glycemic index components and is stable at fluctuations of temperature and pH when used in food and health care composition.

It is been further observed that a person suffering from diabetes has a reduced potent insulin secreting centers in the pancreas, rendering poor availability of insulin for the degradation of carbohydrates. This results in slower degradation of carbohydrates and the blood sugar concentration tends to show wide fluctuations. Particularly, high levels of blood sugar concentrations are observed during the first 2-4 hours after eating. Thus, diabetes may cause serious consequences on the normal functioning of the body of the person afflicted thereby, if adequate precautions are not taken to control the blood sugar levels.

Presently diabetes is treated either by the administration of drugs belonging to the class of Sulphonylureas, Biguanides, Thiazolidinediones, Meglitinides, Alpha glucosidase inhibitors or by insulin injections or combination thereof.

The known antidiabetic drugs help stimulating the secretion of active centers in the pancreas attempting to re-equilibrate the insulin balance. However, with continued administration, the deterioration of the active pancreatic islets usually increases and either stronger or higher dosages of these drugs are required. This eventually leads to increased breakdown of the active centers in the pancreas and further administration of an insulin injection is required. Furthermore, insulin administration is associated with an increased risk of diabetes-related complications, cancer, in addition to causing large variations in blood sugar concentrations, usually reaching dangerously high levels of prolonged duration. Moreover, other natural sweetener compositions which include polyols exhibit a laxative effect.

Hence there is a need to develop a nutraceutical composition or a pharmaceutical composition, which addresses these drawbacks, to develop a product which is better and safer for diabetic individuals.

Surprisingly, the inventors have developed a sweetener, a nutraceutical and a pharmaceutical composition which is free from high glycemic bulking agents, and have a pH near to neutral, unlike artificial sweeteners. The composition not only addresses the drawbacks of the known sweetener compositions, but also mimics the sensory profile of sugar and acts as a sugar modulator taking into consideration, the low Glycemic index and low insulin index requirements (practically nil insulin index) of diabetics and people suffering from obesity, metabolic syndromes, cardiovascular diseases, hypertension and substantial lowering of blood sugar levels and HbA1C values in diabetic individuals. Again, the sweetener composition of the invention eliminates the laxative effect observed with the consumption of other known sweetener compositions which contain polyols. The sweetener and the nutraceutical composition is therefore highly safe not only for diabetics but also for children and pregnant women. Furthermore, the pharmaceutical composition of the invention is highly effective in controlling blood sugar, oxidative stress, HbA1C values, cholesterol levels, triglyceride levels and several other disease indications.

SUMMARY OF THE INVENTION

In a first aspect, the invention relates to glucose oxidase compositions i.e. compositions having glucose oxidase enzyme as a primary ingredient, Glucose oxidase compositions contain from 0.01 to 95% of glucose oxidase enzyme. The additional ingredients make up at least 5% of the composition and include one or more of a carbohydrate, polyol or sugar alcohol.

In an embodiment, the additional ingredient is a carbohydrate. In yet another embodiment, carbohydrate is a dietary fibre. In yet another embodiment, carbohydrate is a saccharide.

Invention further includes further compositions prepared from glucose oxidase compositions. Glucose oxidase compositions are incorporated into further compositions such as food compositions including compositions for fortification of food, sweetener compositions, nutraceutical compositions and pharmaceutical compositions.

Glucose oxidase compositions and further compositions can be formulated into various solid and liquid dosage forms. For example, they can be given in hard or soft capsule or tabletted into tablets or provided in the form of sachets and kits thereof. Some of the forms include Powder composition, granule compositions, crystalline compositions, pellet, pill, tablet, hard and soft capsule compositions, pellet compositions, powder for oral suspensions, liquid solutions and suspensions and sterile preparation and kits.

In a second aspect, the invention relates to further compositions such as sweetener compositions produced from glucose oxidase compositions. These sweetener compositions preferably contain at least 10% of sweetening agent. In this aspect, the sweetener compositions are developed as modified sugar. Modified sugars have higher amounts of sweetening agent preferably at least 50%, more preferably at least 60% and most preferably at least 70%.

In a third aspect, the invention relates to further compositions such as food compositions produced from glucose oxidase compositions. The glucose oxidase compositions having glucose oxidase and at least one carbohydrate, polyols or sugar alcohols can be used to prepare further food compositions such as biscuits, confectionaries, bakery products, beverages, juices, products made from fruits or vegetables, sauces, jams, jellies, ready to eat foods, ready to cook foods, sweets and deserts etc. The preferred additional ingredient is carbohydrate, more preferably dietary fibre. In this aspect, the glucose oxidase compositions are used for fortification of food such as they may be added to food products such as wheat flour, semolina, maize flour, rice flour and any similar food component to fortify the same with glucose oxidase composition.

In a fourth aspect, the invention relates to further compositions such as nutraceutical compositions produced from glucose oxidase compositions. Such nutraceutical compositions comprise of one or more of digestive enzymes, antioxidants, nucleotides or nucleic acids, vitamins, minerals, essential and non-essential amino acids and branched chain amino acids (BCAA) as well as speciality nutraceuticals like glutathione, Human growth hormone (HGH), N-acetyl cysteine. The preferred branched chain amino acids are Leucine, Isoleucine, Valine, Speciality nutraceuticals selected from one or more of Glutathione, Human growth hormone (HGH), N-acetyl cysteine, S Adenosyl L-Methionine (SAMe).

In a fifth aspect, the invention relates to further compositions such as pharmaceutical compositions produced from glucose oxidase compositions. These compositions have pharmaceutical active ingredients useful for treating one or more of hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's symptoms and Parkinson's disease In an embodiment, glucose oxidase composition having up to 95% of glucose oxidase can be added to prepare further pharmaceutical composition having insulin, sulfonylureas, biguanides gliptins etc.

Addition of glucose oxidase compositions to anti-diabetic compositions are preferred. Apart from anti-diabetics, glucose oxidase compositions are combined with other medicines such as anti-hypertensives and medicines used for treatment of elevated total cholesterol, LDL, triglycerides, and to elevate HDL cholesterol etc. and also medicines for Alzheimer's symptoms and Parkinson's disease.

The glucose oxidase helps to reduce the dose of medicine and also the frequency and duration of the medicine.

In another aspect, the invention relates to providing glucose oxidase compositions or further compositions to provide health benefit to individuals for maintaining blood sugar level, cholesterol and triglyceride levels and body weight within normal limit. Further individuals on such treatment have other health benefit such as high energy levels throughout the day.

In yet another aspect, the invention relates to providing health benefit to individuals suffering from one or more of following:
hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's and Parkinson's disease.

It is surprisingly observed by the inventors of the present invention that glucose oxidase compositions and further compositions provide large number of benefits to any individual regardless of age, sex, health, fitness status. Even in healthy normal individuals, glucose oxidase compositions and further compositions provide several health benefits such as maintenance of correct blood sugar levels and body weight and boosting energy levels etc.

DESCRIPTION OF THE INVENTION

In a first aspect, the invention relates to glucose oxidase compositions i.e. compositions having glucose oxidase enzyme as a primary ingredient, Glucose oxidase compositions contain from 0.01 to 95% of glucose oxidase enzyme. The additional ingredients make up at least 5% of the composition and include one or more of a carbohydrate, polyol or sugar alcohol.

In an embodiment, the additional ingredient is a carbohydrate. In yet another embodiment, carbohydrate is a dietary fibre. In one more embodiment, carbohydrate is a saccharide.

In one more embodiment, an additional ingredient is a polyol or a sugar alcohol selected from one or more of mannitol, xylitol, maltitol, isomalt, inositol, erythritol, lactitol, glycerol (glycerine), sorbitol, arabitol, ribitol, polyglycetol, hydrogenated starch hydrolysates and its derivatives (HSH), threitol, fruitol, iditol, volemitol, lactitol, galactitol, palatinose, palatinit, propylene glycol, reduced isomalto-oligosaccharides, fructooligosaccharide, maltooligosaccharide, reduced xylo-oligosaccharides, reduced gentiooligosaccharides, reduced maltose syrup, reduced glucose syrup, reduced starch sugar and combinations thereof.

In one more embodiment, an additional ingredient is a saccharide selected from one or more of tagatose, rhamnose, dextrin including cyclodextrin such as α-cyclodextrin, β-cyclodextrin, and γ-cyclodextrin), maltodextrin (including resistant maltodextrins such as Dietary fibersol-2™), dextran, ribulose, threose, arabinose, xylose, lyxose, allose, altrose, mannose, idose, levulose, hexulose, maltose, invert sugar, isotrehalose, neotrehalose, palatinose or isomaltulose, erythrose, deoxyribose, gulose, idose, talose, erythrulose, xylulose, psicose, turanose, cellulose, cellobiose, starch, pectins such as amylopectin, glucosamine, mannosamine, fucose, glucuronic acid, gluconic acid, glucono-lactone, glycogen, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructo-oligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup.

In yet another embodiment, an additional ingredient is a dietary fibre selected from one or more of non-starch polysaccharides, methylcellulose, β-glucans, mucilage, waxes, cyclodextrins, celluloses, hemicelluloses, starches, dextrins, inulins, lignins, chitins, pectins, beta-glucans (from oat bran, whole oats, oatrim or rolled oats, whole grain or dry-milled barley), fibres extracted from legumes, Chitosan, natural gums, xanthan gum, guar gum, gellan gum, tara gum, gum acacia, gum arabic, beta-mannan, locust bean gum (carob), psylium seed husk gum, galactomannan, glucomannan or konjac, karaya, tragacanth, hexoses, pentoses, resistant starch, plant waxes, alginic acids (alginates), natriumalginat, kaliumalginat, ammoniumalginat, calciumalginat, propylenglycolalginat, (PGA), agar, carrageen, raffinose, xylose, polydextrose, lactulose, vegetable gums, polysaccharide, heterosaccharides, agar-agar, alginate, oligosaccharides, arabinoxylan (a hemicellulose), fructo-oligosaccharides (FOS, oligofructose), galacto-oligosaccharides (GOS), human milk oligosaccharides (HMO), isomalto-oligosaccharides (IMO), lactosucrose, mannan-oligosaccharides (MOS), raffinose, stachyose, verbascose and derivatives thereof.

Invention further includes further compositions prepared from glucose oxidase compositions. Glucose oxidase compositions are incorporated into further compositions such as food compositions including compositions for fortification of food, sweetener compositions, nutraceutical compositions and pharmaceutical compositions. When further compositions are prepared from glucose oxidase compositions, the process may involve either first preparing glucose oxidase composition and adding further ingredients to make further compositions or without first preparing glucose oxidase compositions but directly preparing further compositions by adding all ingredients of glucose oxidase compositions and further ingredients.

Glucose oxidase compositions and further compositions can be formulated into various solid and liquid dosage forms. For example, they can be given in hard or soft capsule or tabletted into tablets or provided in the form of sachets and kits thereof.

In kits, the components of glucose oxidase composition or further compositions can be present together as a single composition or present as separate components such as in separate sachets. In such cases before consumption, the components are mixed together or added to a third ingredient and consumed. This third ingredient can be food ingredient such as juice. Since the overall concept is about taking glucose oxidase composition over a day, it is also possible that the separate components are consumed within a specified time interval preferably not exceeding 12 hrs and preferably not exceeding 6 hrs.

For example, a nutraceutical composition in a kit form may have glucose oxidase, dietary fibres and vitamins and antioxidants and they are either mixed together and consumed or added to a third ingredient and consumed or are consumed at different times such as breakfast time and a meal time or a meal time and a snack time etc. The time period is not more than 12 hrs and preferably not more than 6 hrs.

In an embodiment as presented in table 1, glucose oxidase composition contains 4% of glucose oxidase and 96% of beta glucan. In another embodiment in table 2, glucose oxidase composition contains 4% of glucose oxidase and 96% of mannitol.

In a second aspect, the invention relates to further compositions such as sweetener compositions produced from glucose oxidase compositions. These sweetener compositions contain at least 10% of sweetening agent. Table 7 provides sweetener compositions from formulations I to VII having at least 10% of one or more of sucrose, mannitol, erythritol and tagatose. Preferably sweetening agent is 15% and above. Most preferably it is 50% and above.

In an embodiment, as presented in table 10, there is provided a sweetener composition without dietary fibre containing 6% Glucose oxidase enzyme+15% Mannitol+ 45% Sucrose+34% Tagatose. This sweetener composition tastes just like sugar without any aftertaste. This contains glucose oxidase composition having around 28.6 parts of glucose oxidase and 71.4 parts of mannitol. This composition in 21 parts is converted into a further sweetener composition by adding 79 parts having 45% sucrose and 34% tagatose. This composition can also be prepared by directly mixing all ingredients together without first making a separate glucose oxidase composition. In this composition replacing 8% mannitol with inulin does not affect the sweetness of the composition and such new composition is a sweetener composition according to the present invention.

In a third aspect, the invention relates to further compositions such as food compositions produced from glucose oxidase compositions. The glucose oxidase compositions having glucose oxidase and at least one dietary fibre can be used to prepare further food compositions such as biscuits, confectionaries, bakery products, beverages, juices, products made from fruits or vegetables, sauces, jams, jellies, ready to eat foods, ready to cook foods, sweets and deserts etc. In this aspect, the glucose oxidase compositions are added to food products such as wheat flour, semolina, maize flour, rice flour and any similar food component to fortify the same with glucose oxidase composition.

In a fourth aspect, the invention relates to further compositions such as nutraceutical compositions produced from glucose oxidase compositions. Such nutraceutical compositions comprise of one or more of dietary fibre, digestive enzymes, antioxidants, nucleotides or nucleic acids, vitamins, minerals, essential amino acids, non-essential amino acids, branched chain amino acids (BCAA), speciality nutraceuticals selected from one or more of glutathione, Human growth hormone (HGH), N-acetyl cysteine and plant and fruit extracts such as pine bark extract, D-Ribose, bilberry Extract, *Costus igneus* (Insulin Plant) extract, cranberry extract, blueberry extract, Gooseberry Extract, Rosemary Extract, *Gymnema Sylvestra*, mangosteen extract, pineapple extract, and kiwi extract and combinations thereof.

The enzymes are one or more of papain, bromelain, Lipase, amylase, Glucoamylase, beta glucanase, Fructosyl Transferase, and combinations thereof.

The branched chain amino acids (BCAA) include one or more of Leucine, Isoleucine, Valine, Speciality nutraceuticals selected from one or more of Glutathione, Human growth hormone (HGH), N-acetyl cysteine, S Adenosyl L-Methionine (SAMe).

In a fifth aspect, the invention relates to further compositions such as pharmaceutical compositions produced from glucose oxidase compositions.

In an embodiment, glucose oxidase composition having up to 95% of glucose oxidase can be added to prepare further pharmaceutical composition having insulin, sulfonylureas, biguanides, gliptins etc.

Apart from anti-diabetics, glucose oxidase compositions are combined with other medicines such as anti-hypertensives and medicines used for treatment of elevated total cholesterol, LDL, triglycerides, and to elevate HDL cholesterol etc.

The glucose oxidase will help to reduce the dose of medicine and also the frequency and duration of the medicine.

In another aspect, the invention relates to providing glucose oxidase compositions or further compositions to provide health benefit to individuals for maintaining blood sugar level, cholesterol and triglyceride levels and body weight within normal limit. Further individuals on such treatment have other health benefit such as high energy levels throughout the day.

In yet another aspect, the invention relates to providing health benefit to individuals suffering from one or more of following:

hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's and Parkinson's disease.

It is surprisingly observed by the inventors of the present invention that glucose oxidase compositions and further compositions provide large number of benefits to any individual regardless of age, sex, health, fitness status. Even in healthy normal individuals, glucose oxidase compositions and further compositions provide several health benefit such as maintenance of correct blood sugar levels and body weight and boosting energy levels etc.

The glucose oxidase compositions and further compositions can be provided in the form of sachets filled with powder, granule and crystalline compositions, pills, pellets or granules in capsule or tablets etc. The dose will be around 1-2 dosage form per day for healthy individuals and 2-4 dosage forms per day for an individual suffering from any diseases mentioned hereinbefore.

To provide that the compositions of present invention do not have any adverse effects on healthy individuals, sweetener compositions incorporating glucose oxidase compositions are tested on healthy individuals and the corresponding blood sugar levels are evaluated. This data is compared with i) glucose tolerance test and ii) similar test conducted with an artificial sweetener composition having sucralose. The data is as provided under table 21 and reflects that the sweetener compositions of the present invention are safer to use even for healthy individuals as compared to artificial sweeteners.

In a second aspect, the invention relates to a sweetener composition comprising: Glucose oxidase (GOD) enzyme composition. The sweetener composition further includes at least one low glycemic index nutritive ingredient with a glycemic index of less than 70, preferably less than 50 Such low glycemic index nutritive ingredient is selected from one or more of carbohydrates, polyols and sugar alcohols. The carbohydrates are selected from one or more of saccharides and dietary fibres. A low glycemic index nutritive ingredient includes a sweetening agent. The sweetener composition preferably includes at least 10% of a sweetening agent of the total composition, more preferably at least 30% of the of a sweetening agent of the total composition and most preferably at least 50% of a sweetening agent of the total composition.

The glucose oxidase composition is present in further compositions in a concentration range of from 0.01%-99.99% by weight of the total composition. Preferably, glucose oxidase enzyme composition is present in further compositions in amount from 0.01%-90% by weight of the total composition. When Glucose oxidase in glucose oxidase composition is from 0.01-95% of the composition. The low glycemic index nutritive ingredient may be present as a part of glucose oxidase composition as well as further compositions. When it is present as a part of both the compositions, its concentration may go up to 99.9% by weight of the total composition.

It has been surprisingly observed that the sweetener composition of the present invention may have low glycemic index and low calorie and ideal for the hyperglycemic patients so that they can enjoy a normal life style The sweetener composition of the present invention can be used exactly like sugar in the same quantity to get the same quality as that of sugar in a variety of foods and processed food products like bakery, confectionery, etc. The sweetener composition of the invention mimics the sensory profile of sugar and acts as a sugar modulator. The composition is developed keeping in mind low Glycemic index and low insulin index requirements (practically nil insulin index) of diabetics and people suffering from obesity, metabolic syndromes, cardiovascular diseases, hypertension and substantial lowering of blood sugar levels and HbA1C values in diabetics.

Sweetener composition according to the present invention can be further developed into a modified sugar. The modified sugars may contain high amounts of sweetening agent preferably at least 50%, more preferably at least 60% and most preferably at least 70%. For example, samples A-D of table 8 are modified sugars having more than 50% of sweetening agent. According to one embodiment, the invention relates to a modified sugar which includes the Glucose oxidase (GOD) enzyme in a concentration range of from 0.1%-50% by weight of the total composition, preferably in the range of from 0.1%-40% and more preferably from 0.1%-30%.

A further embodiment of the invention relates to an article of food which includes food composition is in the form of biscuits, confectionaries, bakery products, beverages, juices, products made from fruits or vegetables, sauces, jams, jellies, ready to eat foods, ready to cook foods, sweets and deserts and food supplements incorporating sweetener compositions.

The sweetener composition containing the Glucose oxidase (GOD) enzyme in a concentration range of from 0.01%-99.99% by weight of the total composition. The article of food further includes a low glycemic index nutritive ingredient with a glycemic index of less than 70. The low glycemic index nutritive ingredient is present in a concentration range of from 0.01%-99.9% by weight of the total composition.

The invention further relates to a nutraceutical composition comprising the sweetener composition which includes the glucose oxidase enzyme and at least one low glycemic index nutritive ingredient. The Glucose oxidase (GOD) enzyme is present in the nutraceutical composition in a concentration range of 0.01%-99.99% by weight of the total composition. The nutritive ingredient comprised in the nutraceutical composition is a low glycemic index compound with a glycemic index of less than 70. The nutritive ingredient is present in a concentration range of 0.01%-99.9% by weight of the total composition.

According to another embodiment, the invention relates to the use of a nutraceutical composition which includes Glucose oxidase (GOD) enzyme for controlling one or more of hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, managing high-density lipoproteins (HDL) and low density lipoproteins (LDL), triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, and neurodegenerative disorders such as cognitive dysfunction, Alzheimer's symptoms and Parkinson's disease. The composition helps in the boosting of cellular energy and muscular respiration. Also, the composition helps in the boosting of cellular energy and muscular respiration.

According to an embodiment, the invention relates to a pharmaceutical composition which includes the active pharmaceutical ingredient, Glucose oxidase (GOD) enzyme and at least one low glycemic index nutritive ingredient with a glycemic index of less than 70. The active pharmaceutical composition contains active pharmaceutical ingredient for controlling one or more of hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, non-proliferative diabetic retinopathy, proliferative diabetic retinopathy, diabetic macular edema, cataract, glaucoma, managing high-density lipoproteins (HDL) and low density lipoproteins (LDL), triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, and neurogenerative disorders such as cognitive dysfunction, Alzheimer's symptoms and Parkinson's disease.

Moreover, the nutraceutical or the pharmaceutical composition of the present invention promotes regulation of the blood sugar concentrations in non-diabetic individuals as well as heavily diabetic individuals. It is further observed that the composition of the invention when ingested co-acts with the insulin normally present in the body to reduce the blood sugar concentrations by direct oxidation of glucose or by increasing the speed of the entire metabolic carbohydrate degradation process. Thus, the compositions of the invention are useful as a food supplement as they potentiate and enhance the effectiveness of the insulin present in the non-diabetic human body. Moreover, the composition effectively controls the blood sugar levels of individuals who are hyperglycaemic. It was surprisingly observed that blood sugar levels of normal individuals does not drop below the minimum threshold and is effectively maintained at a normal level even with the regular consumption of the sweetener composition of the invention which includes the glucose oxidase enzyme. Again, the composition is highly cost effective as compared to conventional antidiabetic compositions available in the market.

Moreover, the sweetener composition of the invention provides a more sugar-like temporal profile including sweetness onset and sweetness linger, along with more sugar-like flavour profile.

In describing the embodiment of the invention, specific terminology is chosen for the sake of clarity. However, it is not intended that the invention be limited to the specific terms so selected and it is to be understood that each specific term includes all technical equivalents that operate in a similar manner to accomplish a similar purpose.

The invention relates to a glucose oxidase compositions and further compositions such as sweetener compositions, food compositions, compositions for fortification of food, nutraceutical compositions and pharmaceutical compositions including Glucose oxidase (GOD) enzyme. These compositions, unless they are food compositions, are administered along with food, before or after food so that glucose is released in the blood and glucose oxidase can act on excess glucose and regulate the same. These compositions can also be provided in kits wherein these compositions are provided as one compositions to be taken multiple times or multiple compositions having different components of the compositions of the present invention. For example, a kit may contain a sachet of dietary fibres and a sachet of glucose oxidase and a sachet of vitamins. Based on the instructions these sachets are used over a day.

Glucose oxidase enzyme (GOD) is chemically identified as .beta.-D-glucopyranose aerodehydrogenase. It is referred to in the Enzyme Handbook, Vol. I (1969) by T. E. Barman with an Enzyme Code as EC 1.1.3.4. It is an enzyme obtained from mycelia of fungi such as Aspergilli, particularly *Aspergillus niger* and Penicillia and is a flavoprotein which catalyzes the oxidation of glucose to gluconic acid, the molecular oxygen being reduced to hydrogen peroxide. A glucose oxidase unit is defined as that quantity of enzyme which will oxidize 1 millimole of B-D-glucose to D-gluconic acid and hydrogen peroxide per minute at pH 5.1 and 35 DEG C. In the presence of excess oxygen, the activity may increase 50-100%. The molecular weight of the product obtained from *Aspergillus Niger* is about 186,000. This enzyme is highly specific for B-D-glucose. The glucose oxidase enzyme used in accordance with the present invention is commercially obtained from manufacturers such as Aum Enzymes as Glucozyme 100 and Novozyme under the brand Gluzyme® Mono 10.000 BG.

The Glucose oxidase (GOD) enzyme is present in a concentration range of from 0.01% to 95% by weight of the total composition. Here total composition means any of the glucose oxidase composition or a further composition. The Glucose oxidase (GOD) enzyme is preferably present in the concentration range of from 0.1% to 40% by weight. According to an embodiment, the glucose oxidase enzyme is present in the concentration range of from 0.1% to 30% by weight of the total composition. According to another embodiment, the glucose oxidase enzyme is present in the concentration range of from 0.1% to 20% by weight of the total composition. According to another embodiment, the glucose oxidase enzyme is present in the concentration range of from 1% to 10% by weight of the total composition. According to another embodiment, glucose oxidase enzyme is present in the concentration range of from 1% to 5% by weight of the total composition.

According to an embodiment, the glucose oxidase enzyme is present in a concentration of at least 0.01% by weight of the total composition. According to an embodiment, the glucose oxidase enzyme is present in a concentration of at least 1% by weight of the total composition. According to an embodiment, the glucose oxidase enzyme is present in a concentration of at least 5% by weight of the total composition. According to an embodiment, the glucose oxidase enzyme is present in a concentration of at least 10% by weight of the total composition. According to an embodiment, the glucose oxidase enzyme is present in a concentration of at least 20% by weight of the total composition. According to an embodiment, the glucose oxidase enzyme is present in a concentration of at least 30% by weight of the total composition. According to an embodiment, the glucose oxidase enzyme is present in a concentration of at least 40% by weight of the total composition. According to an embodiment, the glucose oxidase enzyme is present in a concentration of at least 60% by weight of the total composition. According to an embodiment, the glucose oxidase enzyme is present in a concentration of at least 80% by weight of the total composition. According to an embodiment, the glucose oxidase enzyme is present in a concentration of at least 90% by weight of the total composition. According to an embodiment, the glucose oxidase enzyme is present in a concentration of at least 95% by weight of the total composition.

In further compositions, the low glycemic index nutritive ingredient is present in a concentration range of from 0.01%-99.9% by weight of the total composition. Preferably, the low glycemic index nutritive ingredient is present in a concentration range of from 0.1% to 96% by weight of the composition. According to another embodiment, the low glycemic index nutritive ingredient is present in a concentration range of 1%-90% by weight of the total composition. According to yet another embodiment, the low glycemic index nutritive ingredient is present in a concentration range of 1%-70% by weight of the total composition. According to yet another embodiment, the low glycemic index nutritive ingredient is present in a concentration range of 1%-50% by weight of the total composition. According to yet another embodiment, the low glycemic index nutritive ingredient is present in a concentration range of 1%-30% by weight of the total composition. According to yet another embodiment, the low glycemic index nutritive ingredient is present in a concentration range of 1%-15% by weight of the total composition. According to yet another embodiment, the low glycemic index nutritive ingredient is present in a concentration range of 1%-10% by weight of the total composition. According to yet another embodiment, the low glycemic index nutritive ingredient is present in a concentration range of 1%-10% by weight of the total composition. According to an embodiment, the low glycemic index nutritive ingredient is either a carbohydrate or a polyol or both.

According to an embodiment, the low glycemic index nutritive ingredient used in accordance with the invention is selected from one or more of carbohydrates and polyols or sugar alcohols. The carbohydrates are selected from one or more of dietary fibres and saccharides.

Preferably, the low glycemic index nutritive ingredient has a glycemic index of not more than 60. More preferably, the low glycemic index nutritive ingredient has a glycemic index of not more than 50.

Several carbohydrates which include dietary fibres, saccharides and polysaccharides, which have a low glycemic index are encompassed within the scope of the present invention.

The dietary fibres used in accordance with the present invention are a portion of food that is resistant to hydrolysis by human digestive enzymes. Several carbohydrates having significantly different structures in both composition and linkages fall within the scope of dietary fibres. Non-limiting examples of dietary fibres used according to an embodiment of the present invention include one or more of non-starch polysaccharides, methylcellulose, β-glucans, mucilage, waxes, cyclodextrins, celluloses, hemicelluloses, starches, dextrins, inulins, lignins, chitins, pectins, beta-glucans (from oat bran, whole oats, oatrim or rolled oats, whole grain or dry-milled barley), fibres extracted from legumes, Chitosan, natural gums, xanthan gum, guar gum, gellan gum, tara gum, gum acacia, gum arabic, beta-mannan, locust bean gum (carob), psyllium seed husk gum, galactomannan, glucomannan or konjac, karaya, tragacanth, hexoses, pentoses, resistant starch, plant waxes, alginic acids (alginates), natriumalginat, kaliumalginat, ammoniumalginat, calciumalginat, propylenglycolalginat, (PGA), agar, carrageen, raffinose, xylose, polydextrose, lactulose, vegetable gums, polysaccharide, heterosaccharides, agar-agar, alginate, oligosaccharides, arabinoxylan (a hemicellulose), fructo-oligosaccharides (FOS, oligofructose), galacto-oligosaccharides (GOS), human milk oligosaccharides (HMO), isomalto-oligosaccharides (IMO), lactosucrose, mannan-oligosaccharides (MOS), raffinose, stachyose, verbascose and derivatives thereof.

Inulin comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules.

Food sources of dietary fibres include, but are not limited to, grains, legumes, fruits, and vegetables. Grains providing dietary fibres include, but are not limited to, oats, rye, barley, wheat. Legumes providing dietary fibres include, but are not limited to, peas and beans such as soybeans. Fruits and vegetables providing a source of dietary fibre include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fibres. Parts of plants providing dietary fibres include, but are not limited to, the stems, roots, leaves, seeds, pulp, and skin.

The indigestible animal products such as chitins are also classified as dietary fibres. Sources of dietary fibre often are divided into categories such as soluble dietary fibres and insoluble dietary fibres, based on their solubility in water. Both soluble dietary fibres and insoluble dietary fibres are found in plant foods in varying degrees depending upon the characteristics of the plant. The dietary fibres used herein may include a single dietary fibre or a plurality of dietary fibres.

According to an embodiment, the dietary fibres preferably include at least one of inulins, galactomannan, beta glucan, fibres extracted from legumes, grains, oats, all types of fruits, vegetables and flaxseeds. Preferably the dietary fibres also include Inulins (Oligofructose) from chicory root, pectin from apples, guava, citrus fruits and sunflower heads. Dietary fibres used in accordance with the present invention such inulin and beta glucan are commercially obtained from suppliers such as ADEPT IMPEX PVT. LTD.

The dietary fibres are present in a concentration range of 0.01% to 99.9% by weight of the total composition. According to an embodiment, the dietary fibres are present in a concentration range of 0.1% to 90% by weight of the total composition. According to an embodiment, the dietary fibres are present in a concentration range of 0.1% to 80% by weight of the total composition. According to an embodiment, the dietary fibres are present in a concentration range of 0.1% to 70% by weight of the total composition. According to an embodiment, the dietary fibres are present in a concentration range of 0.1% to 60% by weight of the total composition. According to an embodiment, the dietary fibres are present in a concentration range of 0.1% to 50% by weight of the total composition. According to an embodiment, the dietary fibres are present in a concentration range of 0.1% to 40% by weight of the total composition. According to an embodiment, the dietary fibres are present in a concentration range of 0.1% to 30% by weight of the total composition. According to an embodiment, the dietary fibres are present in a concentration range of 0.1% to 20% by weight of the total composition. According to an embodiment, the dietary fibres are present in a concentration range of 0.1% to 10% by weight of the total composition. According to an embodiment, the dietary fibres are present in a concentration range of 0.1% to 5% by weight of the total composition.

Sugar alcohols, also known as polyols, polyhydric alcohols, or polyalcohols, are the hydrogenated forms of the aldoses or ketoses of a sugar are present in the sweetener or the nutraceutical composition of the present invention. Generally, sugar alcohols can be characterized by the general formula HO—CH2-(CH—OH)n-CH2-OH, wherein n is typically from 1 to 22. For example, when n=2, the sugar alcohol can be erythritol, threitol, etc. For example, when n=3, the sugar alcohol can be arabitol, xylitol, ribitol, etc. For example, when n=4, the sugar alcohol can be mannitol, sorbitol, etc. The most common sugar alcohols have 5 or 6 carbon atoms in their structure, wherein n is 3 or 4, respectively. While sugar alcohols occur naturally, and can be isolated from plants, most often they are obtained by the selective hydrogenation of sugars. An alternative method of producing sugar alcohols is from fermentation of sugars. Sugars generally refer to the aldose or ketose forms of a sugar. Other common sugar alcohols include the monosaccharides erythritol and xylitol and the disaccharides lactitol and maltitol.

The term "polyol", as used herein, refers to a molecule that contains more than one hydroxyl group. A polyol may be a diol, trio, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively.

According to an embodiment, the polyol or sugar alcohols are selected from at least one of mannitol, xylitol, maltitol, isomalt, inositol, erythritol, lactitol, glycerol (glycerine), sorbitol, arabitol, ribitol, polyglycetol, hydrogenated starch hydrolysates (HSH), threitol, fruitol, iditol, volemitol, lactitol, galactitol, palatinose, palatinit, propylene glycol, reduced isomalto-oligosaccharides, fructo-oligosaccharide, maltooligosaccharide, reduced xylo-oligosaccharides, reduced gentio-oligosaccharides, reduced maltose syrup, reduced glucose syrup, reduced starch sugar and sugar alcohols or any other carbohydrates capable of being reduced which does not adversely affect the taste of the sweetener composition.

According to an embodiment, the polyols or sugar alcohols are preferably selected from at least one of mannitol, xylitol, maltitol, erythritol, inositol, isomalt and glycerol. These polyols such as NEOSORB® Sorbitol, LYCASIN® and POLYSORB® maltitol syrup, PEARLITOL® mannitol, SWEETPEARL® maltitol, XYLISORB® xylitol used in accordance with the present invention are commercially available from manufacturers such as Roquette. According to an embodiment, the polyols or sugar alcohols are present in a concentration range of 0.01% to 99.9% by weight of the total composition. According to an embodiment, the polyols or sugar alcohols are present in a concentration range of 0.1% to 90% by weight of the total composition. According to an embodiment, the polyols or sugar alcohols are present in a concentration range of 0.1% to 60% by weight of the total composition. According to an embodiment, the polyols or sugar alcohols are present in a concentration range of 0.1% to 45% by weight of the total composition. According to an embodiment, the polyols or sugar alcohols are present in a concentration range of 0.1% to 30% by weight of the total composition. According to an embodiment, the polyols or sugar alcohols are present in a concentration range of 0.1% to 20% by weight of the total composition. According to an embodiment, the polyols or sugar alcohols are present in a concentration range of 0.1% to 10% by weight of the total composition. According to an embodiment, the polyols or sugar alcohols are present in a concentration range of 0.1% to 5% by weight of the total composition. According to an embodiment, the polyols or sugar alcohols are present in a concentration range of 1%-5% by weight of the total composition.

According to an embodiment, the saccharide is selected from at least one of fructose, glucose, galactose, sucrose, lactose, trehalose, caramel, golden syrup, refiners syrup, blackstrap molasses, maple syrup, honey, sorghum syrup, cane juice, barley malt syrup, coconut palm sugar, brown rice syrup, agave syrup and derivatives thereof. Non limiting examples of saccharides include tagatose, rhamnose, dextrin including cyclodextrin such as α-cyclodextrin, β-cyclodextrin, and γ-cyclodextrin), maltodextrin (including resistant maltodextrins such as Dietary fibersol-2™), dextran, ribulose, threose, arabinose, xylose, lyxose, allose, altrose, mannose, idose, levulose, hexulose, maltose, invert sugar, isotrehalose, neotrehalose, palatinose or isomaltulose, erythrose, deoxyribose, gulose, talose, erythrulose, xylulose, psicose, turanose, cellulose, cellobiose, starch, pectins such as amylopectin, glucosamine, mannosamine, fucose, glucuronic acid, gluconic acid, glucono-lactone, glycogen, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructo-oligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup. The saccharides are present in a concentration range of 0.1% to 99.9% by weight of the total composition. According to another embodiment, the saccharides are present in a concentration range of 1% to 96% by weight of the total composition. According to another embodiment, the saccharides are present in the concentration range of 1% to 90% by weight of the total composition. According to another embodiment, the saccharides are present in a concentration range of 1% to 80% by weight of the total composition. According to another embodiment, the saccharides are present in a concentration range of 1% to 70% by weight of the total composition. According to another embodiment, the saccharides are present in a concentration range of 1% to 60% by weight of the total composition. According to another embodiment, the saccharides are present in a concentration range of 1% to 50% by weight of the total composition. According to another embodiment, the saccharides are present in a concentration range of 1% to 40% by weight of the total composition. According to another embodiment, the saccharides are present in a concentration range of 1% to 30% by weight of the total composition. According to another embodiment, the saccharides are present in a concentration range of 1% to 20% by weight of the total composition. According to another embodiment, the saccharides are present in a concentration range of 1% to 15% by weight of the total composition. According to another embodiment, the saccharides are present in a concentration range of 1% to 10% by weight of the total composition. According to another embodiment, the saccharides are present in a concentration range of 1% to 5% by weight of the total composition.

According to an embodiment, the sweetener composition can include one or more water soluble polysaccharides. The water soluble polysaccharides can be sea weed derived polysaccharides, gum Arabic, galactomannan from fenugreek, alginates, and carrageenan. The water soluble polysaccharides are preferably present in the concentration range up to 10% by weight of the total composition.

According to an embodiment, the saccharides are preferably selected from one or more of glucose, fructose, levulose, hexulose, sucrose, lactose, maltose, fructo-oligosaccharides, starch, dextrin, cellulose, pectin, glycogen, sea weed derived polysaccharides, gum arabic, alginates, carrageenan and galactomannan.

According to another embodiment, the composition of the present invention comprises further actives selected from at least one of digestive enzymes, antioxidants, nucleotides or nucleic acids, vitamins and minerals.

According to an embodiment, the antioxidants include fruit extracts selected from one or more of bilberry extract, cranberry extract, blueberry extract, mangosteen extract, pineapple extract, and kiwi extract. The antioxidants are present in the concentration range up to 30% by weight of the total composition. The antioxidants are preferably present in the concentration range up to 10% by weight of the total composition. According to another embodiment, the antioxidants are present in a concentration range of at least 0.1% by weight of the total composition.

According to an embodiment, the nucleotides are selected from one or more of inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, and their alkali or alkaline earth metal salts, and combinations thereof. The nucleotides described herein may comprise nucleotide-related additives, such as nucleosides or nucleic acid bases (e.g., guanine, cytosine, adenine, thymine, uracil). The nucleotides are present in the concentration range up to 5% by weight of the total composition. The nucleotides are preferably present in the concentration range up to 1% by weight of the total composition. According to another embodiment, the nucleotides are present in a concentration range of at least 0.1% by weight of the total composition.

Vitamins are essential for normal growth and development and also are important for maintaining good health. The vitamins used in accordance with the present invention include vitamin A such as retinol, retinaldehyde, retinoic acid, retinoids, retinal and retitonic acid; Vitamin D or calciferol, chloecalciferol, lumisterol, ergocalciferol, dihydrotachysterol; Vitamin E or tocopherol or tocotrienol; Vitamin K or Phylloquinone or Naphthoquinone; Vitamin B1 or Thiamin; Vitamin B2 or Riboflavin; Vitamin B3 or Niacin or Nicotinic acid or nicotinamide; Vitamin B5 or Pantothenic acid; Vitamin B6 or Pyridoxine or Pyridoxal or Pyridoxamine or pyridoxal hydrochloride; Vitamin B7 or Biotin; Vitamin B9 or folic acid or folate; Vitamin B12 or Cobalamin or cyanocobalamin; Vitamin C or ascorbic acid. Other vitamins may include pseudovitamins such as ubiquinone (coenzyme Q10), pangamic acid, dimethylglycine, taestrile, amygdaline, flavanoids, para-aminobenzoic acid, adenine, adenylic acid, and s-methylmethionine.

Requisite intake of dietary minerals is necessary to maintain health. Minerals, in accordance with the embodiments of the sweetener composition of the invention include bulk minerals required in large amounts or trace minerals needed in relatively small amounts. The bulk minerals include calcium, chlorine, magnesium, phosphorous, potassium, sodium, iodine and sulphur; whereas the trace minerals include chromium, cobalt, copper, fluorine, iron, manganese, molybdenum, selenium, zinc, bismuth, boron, lithium, nickel, rubidium, silicon, strontium, tellurium, tin, titanium, tungsten, and vanadium. The minerals may be in their ionic form or in their molecular form.

According to an embodiment, the vitamins or minerals are present in the concentration range up to 10% by weight of the total composition. According to an embodiment, the vitamins or minerals are present in a concentration range up to 5% by weight of the total composition. According to another embodiment, the vitamins or minerals are present in a concentration of at least 0.1% by weight of the total composition.

The sweetener composition of the invention is prepared by uniformly mixing one or more low glycemic index nutritive ingredients in a rotary batch mixer or any other suitable instrument to obtain a homogenous mixture. To this mixture, requisite quantity of the glucose oxidase enzyme is added and further mixed to obtain the sweetener composition. The composition of the invention can also be prepared in situ by adding the individual components to a non-toxic, edible carrier such as water or food articles for instance puddings, cakes etc.

According to another embodiment, the invention relates to a nutraceutical composition for regulating the blood sugar concentration, for controlling diabetes and other related ailments in the human body. The nutraceutical composition comprises the sweetener composition which includes the Glucose oxidase (GOD) enzyme in a concentration range of 0.01%-99.99% by weight of the total composition. It further includes at least one low glycemic index nutritive ingredient with a glycemic index of less than 70. The low glycemic index nutritive ingredient is present in a concentration range of 0.01%-99.9% by weight of the total composition. According to an embodiment, the low glycemic index nutritive ingredient is either a carbohydrate or a polyol or both. According to another embodiment, the carbohydrates include one or more of saccharides and dietary fibres.

The invention further relates to modified sugar which includes the sweetener composition which comprises Glucose oxidase (GOD) enzyme and at least one nutritive ingredient. The Glucose oxidase enzyme is present in a concentration range of from 0.01%-99.99% by weight of the total composition. The nutritive ingredient has a low glycemic index of less than 70 and is present in a concentration range of from 0.01%-99.9% by weight of the total composition.

According to an embodiment, the invention relates to an article of food which includes the sweetener composition which comprises Glucose oxidase (GOD) enzyme and at least one nutritive ingredient. The Glucose oxidase enzyme is present in a concentration range of from 0.01%-99.99% by weight of the total composition. The low glycemic index nutritive ingredient has a low glycemic index of less than 70 and is present in a concentration range of from 0.01%-99.9% by weight of the total composition.

According to yet another embodiment, the sweetener composition can be used as a table sweetener in place of sugar or other commonly known sweeteners or can be added to various oral or food compositions for improving the sweetness therein in a healthy manner.

The sweetener composition of the invention is low on calories, at par on sweetness when compared to sugar and has good after taste rendering it particularly useful for inclusion in food articles in which sweetness increases their taste while avoiding all the drawbacks associated with sugars and all other known sweetener compositions which have a high glycemic index. Furthermore, the sweetener composition mitigates the drawbacks associated with known sweetener compositions in terms of unpleasant aftertastes or long lingering sweetness.

As used herein, the phrases "sugar-like characteristic," "sugar-like taste," "sugar-like sweet," "sugary," and "sugar-like" are synonymous. Sugar-like characteristics include any characteristic similar to that of sucrose and include, but are not limited to, maximal response, flavour profile, temporal profile, adaptation behaviour, mouthfeel, concentration/response function, taste/and flavour/sweet taste interactions, spatial pattern selectivity, and temperature effects. Of these, however, the flavour profile and temporal profile are particularly important.

According to an embodiment the food products in which the sweetener compositions are used include but are not limited to fruit juices; vegetable juices; fruit beverages; beverages such as tea, coffee, etc; cola drinks; ginger ales; soda waters; other carbonated beverages; health drinks; energy drinks; soft drinks; cocoa; lactic acid bacteria beverages; milk beverages and other general beverages; yogurt; jellies; puddings; cakes; mousse and other desserts; sweet; baked confections; steamed confections; ice creams; sherbets; cold sweets and other ice confectioneries; chewing gums; hard candies; nougat candies; jelly beans; other general confections; fruit flavoured sauces; chocolate sauce and similar sauces; jams; marmalades; breads; ketchups; pouched or packaged or snack foods; instant or ready-to-eat food products; pickles; frozen foods and wide range of processed farm and aquatic products. The invention is useful to fortify variety of food ingredients like rice, wheat flour, lentils, spices, edible oils, salt etc appropriately to enhance the nutritional value of the ingredients and improve metabolism of carbohydrates. The composition can be added to processed foods and beverages, snack foods, ready to eat and cooked foods etc as well other than its usage in herbal and pharmaceutical product formulations.

According to an embodiment, the sweetener composition used in these oral or food products is in an amount which is effective to give the desired sweetness to the food product, and is without any specific limitation. In fact, the sweetness is variable depending on the kind of the food product in which the sweetener composition is added. The dosage is further dependent on other components contained in the food product composition and on the level of sweetness desired by an individual and such other factors. The taste or the sweetness profile of the sweetener composition as compared to sugars or other known natural sweeteners is determined by an expert panel who tastes compositions comprising sugar, other natural sweeteners and compositions comprising the Glucose oxidase enzyme in accordance with the embodiment of the present invention, and provide their conclusions as to the similarities of the characteristics of the compositions containing the glucose oxidase enzyme with other sweeteners or sugar.

According to an embodiment, the sweetener composition is in a solid or liquid form. The solid form includes powder, pill, crystals or tablets. The liquid forms include syrup, elixirs or suspension. According to an embodiment, the sweetener composition is used in at least one of a food composition, beverages and nutraceutical composition.

A further embodiment of the invention relates to a method of regulating or controlling diabetes or blood sugar concentrations in diabetic individuals or persons susceptible to diabetes. The method involves administering the nutraceutical composition comprising Glucose oxidase (GOD) enzyme and, at least one low glycemic index nutritive ingredient with a glycemic index of less than 70 to a person suffering from, or susceptible to diabetes. The nutraceutical composition is administered in an amount sufficient to lower the blood sugar concentration.

According to an embodiment, the nutraceutical composition is in the form of suitable for oral administration such as a liquid, a tablet, a granule or a powder.

According to an embodiment, the inventive nutraceutical composition may be administered either in a single dosage, preferably before the breakfast meal in the morning, or in divided doses, i.e., twice daily or three times daily, preferably before each meal. The inventive composition may be administered in the form of a preformed capsule or a tablet or it may be incorporated in an edible food stuff such as biscuits, etc.

According to an embodiment, the invention further relates to the use of a nutraceutical comprising Glucose oxidase (GOD) enzyme and at least one low glycemic index compound for the controlling hyperglycemia, hypoglycemia, weight loss, obesity, oxidative stress, hyperuricemia, ketoacidosis, nonketotic hyperosmolar coma, cardiovascular diseases, heart stroke, nephropathy, microalbuminuria, insulin resistance, amyloid, foot ulcers, diabetic retinopathy, nonproliferative diabetic retinopathy, proliferative diabetic retinopathy, diabetic macular edema, cataract, glaucoma, high blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovary syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's symptoms and Parkinson's disease.

The nutraceutical composition of the invention is prepared by uniformly mixing one or more low glycemic index compounds in a rotary batch mixer or any other suitable instrument to obtain a homogenous mixture. To this mixture, requisite quantity of the glucose oxidase enzyme is added and further mixed to obtain the nutraceutical composition.

According to an embodiment, the invention further relates to use of a nutraceutical composition comprising Glucose oxidase (GOD) enzyme and the low glycemic index compound for the treatment of non-diabetic ailments such as cognitive dysfunction, Alzheimer's symptoms and Parkinson's disease.

According to an embodiment, the invention further relates to a pharmaceutical composition which includes the Glucose oxidase (GOD) enzyme and at least one low glycemic index nutritive ingredient with a glycemic index of less than 70.

The glucose oxidase enzyme is present in a concentration range of 0.01 to 99.99% by weight of the pharmaceutical composition. According to an embodiment, the Glucose oxidase (GOD) enzyme is present in a concentration range of 0.1% to 40% by total weight of the pharmaceutical composition. According to another embodiment, the Glucose oxidase (GOD) enzyme is present in a concentration range of 0.5% to 20% by total weight of the pharmaceutical composition. According to another embodiment, the Glucose oxidase (GOD) enzyme is present in a concentration range of 1% to 10% by total weight of the pharmaceutical composition.

The pharmaceutical composition further includes a low glycemic index nutritive ingredient which is selected from one or more of carbohydrates, polyols and sugar alcohols. The low glycemic index nutritive ingredient is present in a concentration range of 0.01%-99.9% by total weight of the pharmaceutical composition. According to another embodiment, the low glycemic index nutritive ingredient is present in a concentration range of 0.1% to 90% by weight of the total composition. According to yet another embodiment, the low glycemic index nutritive ingredient is present in a concentration range of 1% to 60% by weight of the total composition. According to yet another embodiment, the low glycemic index nutritive ingredient is present in a concentration range of 1%-30% by weight of the total composition. According to yet another embodiment, the low glycemic index nutritive ingredient is present in a concentration range of 1%-15% by weight of the total composition. According to yet another embodiment, the low glycemic index nutritive ingredient is present in a concentration range of 1%-10% by weight of the total composition. According to an embodiment, the low glycemic index nutritive ingredient includes one or more of carbohydrate and polyols or sugar alcohols. The carbohydrates are selected from one or more of dietary fibres and saccharides.

Preferably, the low glycemic index nutritive ingredient has a glycemic index of not more than 60. More preferably, the low glycemic index nutritive ingredient has a glycemic index of not more than 50.

Non-limiting examples of dietary fibres used in accordance with the pharmaceutical composition include one or more of non-starch polysaccharides, methylcellulose, β-glucans, mucilage, waxes, cyclodextrins, celluloses, hemicelluloses, starches, dextrins, inulins, lignins, chitins, pectins, beta-glucans (from oat bran, whole oats, oatrim or rolled oats, whole grain or dry-milled barley), fibres extracted from legumes, Chitosan, natural gums, xanthan gum, guar gum, gellan gum, tara gum, gum acacia, gum arabic, beta-mannan, locust bean gum (carob), psyllium seed husk gum, galactomannan, glucomannan or konjac, galactomannan, karaya, tragacanth, hexoses, pentoses, resistant starch, plant waxes, alginic acids (alginates), natriumalginat, kaliumalginat, ammoniumalginat, calciumalginat, propylenglycolalginat, (PGA), agar, carrageen, raffinose, xylose, polydextrose, lactulose, vegetable gums, polysaccharide, heterosaccharides, agar-agar, alginate, oligosaccharides, arabinoxylan (a hemicellulose), fructo-oligosaccharides (FOS, oligofructose), galacto-oligosaccharides (GOS), human milk oligosaccharides (HMO), isomalto-oligosaccharides (IMO), lactosucrose, mannan-oligosaccharides (MOS), raffinose, stachyose, verbascose and derivatives thereof.

According to an embodiment, the dietary fibres used in accordance with the pharmaceutical composition includes at least one of inulin, galactomannan, beta glucan, fibres extracted from legumes, grains, oats, all types of fruits, vegetables and flaxseeds. Preferably the dietary fibres also include Inulins (Oligofructose) from chicory root, pectin from apples, guava, citrus fruits and sunflower heads.

The dietary fibres are present in a concentration range of 0.01% to 99.9% by total weight of the pharmaceutical composition. According to an embodiment, the dietary fibres are present in a concentration range of 0.1% to 80% by total weight of the pharmaceutical composition. According to an embodiment, the dietary fibres are present in a concentration range of 0.1% to 60% by total weight of the pharmaceutical composition. According to an embodiment, the dietary fibres are present in a concentration range of 0.1% to 40% by total weight of the pharmaceutical composition. According to an embodiment, the dietary fibres are present in a concentration range of 0.1% to 20% by total weight of the pharmaceutical composition. According to an embodiment, the dietary fibres are present in a concentration range of 0.1% to 10% by weight of the total composition.

According to an embodiment, the polyol or sugar alcohols used in accordance with the pharmaceutical composition include one or more of mannitol, xylitol, maltitol, isomalt, inositol, erythritol, lactitol, glycerol (glycerine), sorbitol, arabitol, ribitol, polyglycetol, hydrogenated starch hydrolysates (HSH), threitol, fruitol, iditol, volemitol, lactitol, galactitol, palatinose, palatinit, propylene glycol, reduced isomalto-oligosaccharides, fructo-oligosaccharide, maltooligosaccharide, fructo-oligosaccharide, maltooligosaccharide, reduced xylo-oligosaccharides, reduced gentio-oligosaccharides, reduced maltose syrup, reduced glucose syrup, reduced starch sugar and sugar alcohols or any other carbohydrates capable of being reduced which does not adversely affect the stability or taste of the pharmaceutical composition.

According to an embodiment, the polyols or sugar alcohols are preferably selected from at least one of mannitol, xylitol, maltitol, erythritol, inositol, isomalt and glycerol. According to an embodiment, the polyols or sugar alcohols are present in a concentration range of 0.01% to 99.9% by total weight of the pharmaceutical composition. According to an embodiment, the polyols or sugar alcohols are present in a concentration range of 0.1% to 60% by total weight of the pharmaceutical composition. According to an embodiment, the polyols or sugar alcohols are present in a concentration range of 0.1% to 30% by total weight of the pharmaceutical composition. According to an embodiment, the polyols or sugar alcohols are present in a concentration range of 0.1% to 10% by total weight of the pharmaceutical composition. According to an embodiment, the polyols or sugar alcohols are present in a concentration range of 0.1% to 5% by total weight of the pharmaceutical composition.

According to an embodiment, the saccharide used in accordance with the pharmaceutical composition includes one or more of fructose, glucose, galactose, sucrose, lactose, trehalose, caramel, golden syrup, refiners syrup, blackstrap molasses, maple syrup, honey, sorghum syrup, cane juice, barley malt syrup, coconut palm sugar, brown rice syrup, agave syrup and derivatives thereof. Non limiting examples of saccharides include tagatose, rhamnose, dextrin including cyclodextrin such as α-cyclodextrin, β-cyclodextrin, and γ-cyclodextrin), maltodextrin (including resistant maltodextrins such as Dietary fibersol-2™) dextran, ribulose, threose, arabinose, xylose, lyxose, allose, altrose, mannose, idose, levulose, hexulose, maltose, invert sugar, isotrehalose, neotrehalose, palatinose or isomaltulose, erythrose, deoxyribose, gulose, idose, talose, erythrulose, xylulose, psicose, turanose, cellulose, cellobiose, starch, pectins such as amylopectin, glucosamine, mannosamine, fucose, glucuronic acid, gluconic acid, glucono-lactone, glycogen, abequose, galactosamine, beet oligosaccharides, isomalto-oligosaccharides (isomaltose, isomaltotriose, panose and the like), xylo-oligosaccharides (xylotriose, xylobiose and the like), gentio-oligoscaccharides (gentiobiose, gentiotriose, gentiotetraose and the like), sorbose, nigero-oligosaccharides, palatinose oligosaccharides, fucose, fructo-oligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), coupling sugars, soybean oligosaccharides, and glucose syrup.

The saccharides are present in a concentration range of 0.01% to 99.9% by total weight of the pharmaceutical composition. According to another embodiment, the saccharides are present in a concentration range of 1% to 80% by total weight of the pharmaceutical composition. According to another embodiment, the saccharides are present in a concentration range of 1% to 60% by total weight of the pharmaceutical composition. According to another embodiment, the saccharides are present in a concentration range of 1% to 40% by total weight of the pharmaceutical composition. According to another embodiment, the saccharides are present in a concentration range of 1% to 20% by total weight of the pharmaceutical composition. According to another embodiment, the saccharides are present in a concentration range of 1% to 10% by total weight of the pharmaceutical composition. According to another embodiment, the saccharides are present in a concentration range of 1% to 5% by total weight of the pharmaceutical composition.

According to an embodiment, the invention further relates to the use of the pharmaceutical composition for controlling hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, nonproliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's symptoms and Parkinson's disease.

According to an embodiment, the pharmaceutical composition can be administered in various forms including solid, liquid or semi-solid forms. The solid forms include granules, powders, tablets, pills, capsules or gel-capsules. The liquid forms include syrups, elixirs and liquid solutions or suspensions. The semi-solid forms may include gels or pastes.

The pharmaceutical active ingredient is selected from one or more of antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, antiinflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarial s, anthelmintics, antiprotozoal, antiserums, vaccines, interferons, tonics, vitamins, cytotoxic drugs, sex hormones, aromatase inhibitors, somatostatin inhibitors, and combinations thereof.

According to another embodiment, the invention also relates to a method of treatment of diseases including hyperglycemia, hypoglycemia, weight management challenges, obesity, oxidative stress, hyperuricemia, ketoacidosis, non-ketotic hyperosmolar coma, cardiovascular disease, heart stroke, nephropathy, microalbuminuria, insulin resistance, amyloid foot ulcers, diabetic retinopathy, nonproliferative diabetic retinopathy, proliferative diabetic retinopathy, diabetic macular edema, cataract, glaucoma, High blood cholesterol (HDL) and LDL, triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's symptoms and Parkinson's disease by administering a sweetener composition or a nutraceutical composition or a pharmaceutical composition comprising glucose oxidase enzyme and at least one low glycemic index nutritive compound to a person suffering from, or susceptible to diabetes.

The present invention will be illustrated in more detail with reference to the following preparation examples and test examples. As will be recognized by one skilled in the art, these examples are just illustrative and are not meant to be limiting.

The following examples illustrate the basic methodology and versatility of the composition of the invention.

Preparation Example 1

Compositions containing Glucose oxidase enzyme (GOD) with additional ingredient in amounts at least 5% and without additional ingredient for the purpose of comparison dietary fibres (inulin and beta glucan)

TABLE 1

| | Glucose oxidase compositions | | | | | | | |
|---|---|---|---|---|---|---|---|---|
| Ingredients | I (wt %) | II (wt %) | III (wt %) | IV (wt %) | V (wt %) | VI (wt %) | VII (wt %) | VIII (wt %) |
| Glucose Oxidase Enzyme | 0.5 | 2 | 4 | 10 | 40 | 80 | 99.99 | 100 |
| Inulin | 50 | 50 | — | 45 | 40 | 10 | 0.01 | 0 |
| Beta Glucan | — | 10 | 96 | 5 | — | — | — | 0 |
| Galactomannan from Fenugreek | 49.5 | 10 | — | 30 | 10 | 10 | — | 0 |
| Wheat bran fibre | — | 28 | — | 10 | 10 | — | — | 0 |

Compositions of samples I to VI are glucose oxidase compositions. Compositions of samples VII and VIII are prepared for comparisons only. Sample I was prepared by uniformly mixing 500 gms of Inulin and 495 gms of Galactomannan obtained from fenugreek, in a rotary batch mixer at 24 degrees Celsius. To this mixture, 5 gms of glucose oxidase enzyme was added and further mixed to obtain a sweetener composition containing 0.5% of Glucose oxidase enzyme, 50% of Inulin and 49.5% of Galactomannan Samples II to VIII were prepared as per the process of preparation of Sample 1 wherein the samples included Glucose Oxidase Enzyme in combination with one or more of inulin, beta glucan, galactomannan from Fenugreek and Wheat bran fibre in concentrations as set forth in Table 1

Example 2

Compositions containing Glucose oxidase enzyme (GOD) and + polyols (mannitol, erythritol, sorbitol and xylitol):

TABLE 2

| | Glucose oxidase compositions | | | | | | | | |
|---|---|---|---|---|---|---|---|---|---|
| Ingredients | I (wt %) | II (wt %) | III (wt %) | IV (wt %) | V (wt %) | VI (wt %) | VII (wt %) | VIII (wt %) | IX (wt %) |
| Glucose Oxidase Enzyme | 0.5 | 2 | 4 | 8 | 10 | 20 | 60 | 80 | 99.99 |
| Mannitol | 30 | 20 | 96 | — | 30 | 10 | — | — | 0.01 |
| Erythritol | 30 | 25 | — | 40 | 5 | 10 | — | 10 | — |
| Sorbitol | 39.5 | 25 | — | — | 45 | 50 | 30 | 10 | — |
| Xylitol | — | 28 | — | 52 | 10 | 10 | 10 | — | — |

Compositions of samples I to VIII are glucose oxidase compositions. Composition of samples IX is prepared for comparisons only. Sample I was prepared by uniformly mixing 300 gms of mannitol, 300 gms of Erythritol and 395 gms of sorbitol in a rotary batch mixer at 24 degrees Celsius. To this mixture, 5 gms of glucose oxidase enzyme was added and further mixed to obtain a sweetener composition containing 0.5% of Glucose oxidase enzyme, 30% of Mannitol, 30% Erythritol and 39.5 of sorbitol.

Samples II to IX were prepared as per the process of preparation of Sample 1 wherein the samples included Glucose Oxidase Enzyme in combination with one or more of mannitol, erythritol, sorbitol and xylitol in concentrations, as set forth in Table 2.

Example 3

Compositions containing Glucose oxidase enzyme (GOD) and + Saccharides (fructose, sucrose, dextrin, sea weed derived polysaccharides, amylopectin):

TABLE 3

Glucose oxidase compositions

| Ingredients | I (wt %) | II (wt %) | III (wt %) | IV (wt %) | V (wt %) | VI (wt %) | VII (wt %) | VIII (wt %) | IX (wt %) |
|---|---|---|---|---|---|---|---|---|---|
| Glucose Oxidase Enzyme | 0.5 | 2 | 6 | 8 | 10 | 20 | 40 | 80 | 99.99 |
| Fructose | 45 | 20 | 94 | — | — | — | 10 | — | 0.01 |
| Sucrose | — | 15 | — | 20 | — | 10 | — | — | — |
| Dextrin | 54.5 | 25 | — | 15 | 40 | 10 | — | 10 | — |
| Lactose | — | 10 | — | 5 | 40 | 50 | 10 | 10 | — |
| Tagatose | — | 18 | — | 52 | 10 | 10 | 40 | — | — |

Compositions of samples I to VIII are glucose oxidase compositions. Composition of samples IX is prepared for comparisons only. Sample I was prepared by uniformly mixing 450 gms of fructose and 545 gms of dextrin in a rotary batch mixer at 24 degrees Celsius. To this mixture, 5 gms of glucose oxidase enzyme was added and further mixed to obtain a sweetener composition containing 0.5% of Glucose oxidase enzyme, 45% of Fructose and 54.5% of dextrin.

Samples II to IX were prepared as per the process of preparation of Sample 1 wherein the samples included Glucose Oxidase Enzyme in combination with one or more of Fructose, sucrose, dextrin, lactose and Tagatose in concentrations, as set forth in Table 3.

Example 4

Compositions containing Glucose oxidase enzyme (GOD), dietary fibres (inulin or beta glucan) and polyols or sugar alcohols (mannitol or erythritol)

TABLE 4

Glucose oxidase composition

| Ingredients | I (wt %) | II (wt %) | III (wt %) | IV (wt %) | V (wt %) | VI (wt %) | VII (wt %) | VIII (wt %) |
|---|---|---|---|---|---|---|---|---|
| Glucose Oxidase Enzyme | 0.5 | 4 | 6 | 10 | 20 | 60 | 80 | 99 |
| Inulin | 45 | 70 | — | — | 25 | — | 10 | 0.5 |
| Beta glucan | 20 | — | 65 | 65 | 25 | 20 | — | — |
| Mannitol | 31 | 26 | 14 | — | 15 | — | 10 | 0.5 |
| Erythritol | 3.5 | — | 15 | 25 | 15 | 20 | — | — |

Compositions of samples I to VII are glucose oxidase compositions. Composition of samples VIII is prepared for comparisons only. To this mixture, 5 gms of glucose oxidase enzyme was added and further mixed to obtain a sweetener composition containing 0.5% of Glucose oxidase enzyme, 45% of inulin, 31% of mannitol and 3.5% of erythritol.

Samples II to VIII were prepared as per the process of preparation of Sample 1 wherein the samples included Glucose Oxidase Enzyme in combination with one or more of inulin and beta glucan and one or more of mannitol and erythritol in concentrations, as set forth in Table 4.

Example 5

Compositions containing Glucose oxidase enzyme (GOD), dietary fibres (inulin or beta glucan) and saccharides (sucrose or sea weed derived polysaccharides)

TABLE 5

| | Sweetener composition | | | | | | | |
|---|---|---|---|---|---|---|---|---|
| Ingredients | I (wt %) | II (wt %) | III (wt %) | IV (wt %) | V (wt %) | VI (wt %) | VII (wt %) | VIII (wt %) |
| Glucose Oxidase Enzyme | 0.5 | 2 | 4 | 8 | 10 | 40 | 80 | 99.99 |
| Inulin | 2 | 1 | — | 35 | — | — | 15 | — |
| Beta glucan | — | 1 | 15 | 10 | 50 | 20 | — | — |
| Sucrose | 94 | — | 41 | 10 | — | — | 5 | — |
| Tagatose | 3.5 | 96 | 40 | 37 | 40 | 40 | — | 0.01 |

Compositions of samples I to VII are glucose oxidase compositions. Composition of samples VIII is prepared for comparisons only. Sample I was prepared by uniformly mixing 20 gms of inulin, 940 gms of sucrose and 35 gms of Sea weed based polysaccharides in a rotary batch mixer at 24 degrees Celsius to obtain a mixture. To this mixture, 5 gms of glucose oxidase enzyme was added and further mixed to obtain a sweetener composition containing 0.5% of Glucose oxidase enzyme, 2% of inulin, 94% of sucrose and 3.5% of the Tagatose.

Samples II to VIII were prepared as per the process of preparation of Sample 1 wherein the samples included Glucose Oxidase Enzyme in combination with one or more of inulin and beta glucan and one or more of sucrose and tagatose in concentrations, as set forth in Table 5.

Example 6

Compositions containing Glucose oxidase enzyme (GOD), polyols such as mannitol or erythritol and saccharides such as sucrose or sea weed derived polysaccharides.

TABLE 6

| | Sweetener compositions | | | | | | | |
|---|---|---|---|---|---|---|---|---|
| Ingredients | I (wt %) | II (wt %) | III (wt %) | IV (wt %) | V (wt %) | VI (wt %) | VII (wt %) | VIII (wt %) |
| Glucose Oxidase Enzyme | 0.5 | 2 | 6 | 10 | 20 | 60 | 80 | 99 |
| Mannitol | 1 | — | 15 | — | — | 10 | 5 | 0.5 |
| Erythritol | 1 | 2 | — | 50 | 20 | — | — | — |
| Sucrose | 95 | — | 45 | — | 40 | 30 | 15 | 0.5 |
| Tagatose | 2.5 | 96 | 34 | 40 | 20 | — | — | — |

Compositions of samples I to VII are glucose oxidase compositions. Composition of samples VIII is prepared for comparisons only. Sample I was prepared by uniformly mixing 10 gms of mannitol, 10 gms of erythritol, 950 gms of sucrose and 25 gms of Sea weed based polysaccharides in a rotary batch mixer at 24 degrees Celsius to obtain a mixture. To this mixture, 5 gms of glucose oxidase enzyme was added and further mixed to obtain a sweetener composition containing 0.5% of Glucose oxidase enzyme, 1% of mannitol, 1% of erythritol, 95% of sucrose and 2.5% of tagatose.

Samples II to VIII were prepared as per the process of preparation of Sample 1 wherein the samples included Glucose Oxidase Enzyme in combination with one or more of mannitol and erythritol one or more of sucrose and tagatose in concentrations, as set forth in Table 6.

Example 7

Compositions containing Glucose oxidase enzyme (GOD), dietary fibres such as inulins and betaglucans, polyols such as mannitol or erythritol and saccharides such as sucrose or tagatose

TABLE 7

| | Sweetener compositions | | | | | | | |
|---|---|---|---|---|---|---|---|---|
| Ingredients | I | II | III | IV | V | VI | VII | VIII |
| | Concentration in weight percentage | | | | | | | |
| Glucose Oxidase Enzyme | 0.5 | 2 | 6 | 8 | 10 | 40 | 80 | 99 |
| Inulin | 5 | 4 | 10 | — | 25 | 30 | 5 | 0.2 |
| Beta glucan | — | 4 | 15 | 30 | 50 | 5 | — | — |
| Mannitol | 1 | 5 | 25 | — | 5 | 5 | 5 | 0.5 |
| Erythritol | 4 | 5 | 20 | 25 | — | — | — | — |
| Sucrose | 80 | 50 | 24 | — | 10 | — | 10 | 0.3 |
| Tagatose | 9.5 | 30 | — | 37 | — | 10 | — | — |

Compositions of samples I to VII are glucose oxidase compositions. Composition of samples VIII is prepared for comparisons only. Sample I was prepared by uniformly mixing 50 gms of inulin, 10 gms of mannitol, 40 gms of erythritol, 800 gms of sucrose and 95 gms of Sea weed based polysaccharides in a rotary batch mixer at 24 degrees Celsius to obtain a mixture. To this mixture, 5 gms of glucose oxidase enzyme was added and further mixed to obtain a sweetener composition containing 0.5% of Glucose oxidase enzyme, 5% inulin, 1% of mannitol, 4% of erythritol, 80% of sucrose and 9.5% of tagatose.

Samples II to VIII were prepared as per the process of preparation of Sample 1 wherein the samples included Glucose Oxidase Enzyme in combination with one or more of inulin and beta glucan; one or more of mannitol and erythritol, one or more of sucrose and sea weed based polysaccharides in concentrations, as set forth in Table 7.

Example 8

Preparation example of Nutraceutical and Sweetener compositions modified sugar containing the glucose oxidase enzyme based sweetener compositions:

TABLE 8

Modified sugars

| Sr. No | Ingredients | Sample A (wt %) | Sample B (wt %) | Sample C (wt %) | Sample D (wt %) | Sample E (wt %) | Sample F (wt %) | Sample G (wt %) |
|---|---|---|---|---|---|---|---|---|
| 1 | Xylitol | 30 | 55 | 20 | 30 | 0 | 30 | 30 |
| 2 | Cranberry extract/fruit extract | 0 | 0 | 0 | 2 | 10 | 0 | 0 |
| 3 | Bilberry extract | 0 | 0 | 5 | 3 | 10 | 0 | 0 |
| 4 | Inulin | 10 | 15 | 2 | 5 | 12 | 15 | 0 |
| 5 | Fenugreek galactomannan | 2 | 0 | 0 | 0 | 18 | 0 | 5 |
| 6 | Beta glucans | 0 | 0 | 7 | 10 | 20 | 0 | 0 |
| 7 | Beta d fructose | 0 | 20 | 64 | 0 | 0 | 15 | 50 |
| 8 | Glucose oxidase enzyme | 5 | 10 | 2 | 10 | 30 | 40 | 15 |
| 9 | Sugar | 53 | 0 | 0 | 40 | 0 | 0 | 0 |
|  | Total | 100 | 100 | 100 | 100 | 100 | 100 | 100 |

TABLE 9

Modified sugars

| Sr. No. | Composition | Sample H (wt %) | Sample I (wt %) | Sample J (wt %) | Sample K (wt %) |
|---|---|---|---|---|---|
| 1 | Xylitol | 15 | 30 | 45 | 40 |
| 2 | Erythritol | 10 | 5 | 0 | 20 |
| 3 | Lactitol | 5 | 0 | 5 | 0 |
| 4 | Inulin | 5 | 15 | 2 | 10 |
| 5 | Maltitol | 2 | 0 | 4 | 0 |
| 6 | Beta Glucan | 0 | 0 | 7 | 10 |
| 7 | Levulose | 58 | 40 | 35 | 0 |
| 8 | Glucose oxidase Enzyme | 5 | 10 | 2 | 20 |
|  | Total | 100 | 100 | 100 | 100 |

Modified sugar as per the sample A was prepared by blending thoroughly all the ingredients as per table 8 in a Nauta mixer or Rotary octagonal blender for 30 mins. The blending is preferably done in an air conditioned room where temperature is less than 24° C. and R.H. is less than 40%. Other samples B-K for the modified sugar were prepared following the process similar to Sample A. Samples E and F are not as sweet as other samples. Hence at least 50% sweetening agent is desired for modified sugar.

Efficacy Data for the Sweetener Composition

Example 9: Sweetness Levels and after Taste Comparisons

A method of evaluation is provided as follows. In this method, none of the samples were swallowed. All samples were expectorated and the mouth was rinsed with water after the tasting. All the samples were tasted by distributing 10 ml of the sample quickly throughout the oral cavity and sweetness intensity was measured. This intensity was measured on a scale of 0-5 where 0 is defined as no perceptible sweetness and 5 was defined as the sweetness of sugar. When maximum sweetness was experienced, the sample was expectorated and the mouth was rinsed with water and rate of "Sweetness Linger" was measured, at 3-4 mins after the water rinse. The sweetness linger was defined using the following scale: 0=no sweetness linger, 1=very slight sweetness linger, 2=slight sweetness linger, 3=moderate sweetness linger, 4=moderately high sweetness linger, 5=high sweetness linger/Not acceptable sweetness. After the sample tasting was completed, it was followed by a water rinse.

All the samples were tasted using the above method by maintaining sufficient time between the samples.

The results were tabulated as follows:

TABLE 10

Taste characteristics of Sweetener compositions

| Sample No | Example | Sweetness value | Sweetness index | After-taste | Sweetness Linger |
|---|---|---|---|---|---|
| 1. | 6% Glucose oxidase enzyme + 15% Mannitol (or 8% inulin and 7% mannitol) + 45% Sucrose + 34% Tagatose containing sweetener composition according to an embodiment | Sweet like sugar | 5 | No | 0 |

TABLE 10-continued

Taste characteristics of Sweetener compositions

| Sample No | Example | Sweetness value | Sweetness index | Aftertaste | Sweetness Linger |
|---|---|---|---|---|---|
| | of the present invention | | | | |
| 2. | 20% Glucose oxidase enzyme + 20% erythritol + 40% sucrose + 20% Tagatose containing sweetener composition according to an embodiment of the present invention | Sweet like sugar | 5 | No | 0 |
| 3. | Sugar | Sweet | 5 | No | 0 |
| 4. | Glucose | Less sweet than sugar | 2 | No | 0 |
| 5. | Splenda (Sucralose + Maltodextrin 95% + Dextrose) | About 600 times sweet than sugar | 3 | Lingering sweetness, Sweet aftertaste | 4 |
| 6 | Acesulfame K containing artificial sweetener with 6% chitosan, sucrose and sorbitol as per US '439 | 180-200 times sweeter than sugar | 900-1000 | Slight aftertaste, astringent | 2 |
| 7. | Stevia (natural sugar substitute) containing sweetener with 6% chitosan, sucrose and sorbitol as per US '439 | 30-300 times sweeter than sugar | 150-1500 | Bitter astringent | 5 |
| 8. | Control | Sweet | 5 | No aftertaste | 0 |

It can be observed from the above table that samples 1 and 2 containing glucose oxidase enzyme prepared as per the embodiment of the present invention exhibits a sweetness index of 5 and tastes exactly similar to that of sugar as compared to Sample 3 containing glucose and Samples 4 and 5 which include artificial sweeteners such as Splenda, which is a Sucralose containing sweetener and Acesulfame K, or Sample 6 which include natural sugar substitute such as *Stevia*, respectively. In fact, it can be seen that these artificial sweeteners are 30-200 times more sweeter as compared to that of sugar. Further, it was observed that the artificial sweeteners Acesulfame K or sweeteners with natural sugar substitute such as *Stevia* exhibited a bitter astringent like after taste whereas Sucralose exhibited a sweet aftertaste which lingered for a quite long time. It was surprising to observe that the GOD containing sweetener composition as per the embodiment of the present invention not only demonstrated sweetness equivalent to that to sugar but also did not exhibit any unpleasant after-taste or sweetness linger after consumption as compared to other known sweeteners.

Example: 10

Efficacy of the Sweetener or the Nutraceutical Composition in Controlling Body Weight in Individuals:

Six type 2 diabetic patients were randomly administered the Glucose oxidase containing sweetener composition as per the embodiment of the present invention for 3 weeks, 5 patients were administered sugar and compositions containing natural sugar substitute (*stevia* based) based sweeteners, or artificial sweeteners based on Sucralose or Acem or compositions containing dietary fibres with saccharides, dietary fibres with sugar alcohols and dietary fibres with sugar alcohols and saccharides, the details of which are as set forth in the Table below. One patient was not given any composition. Before the onset of the study (week 0) and after 2 months, weight measurements were taken. The results are as tabulated below:

TABLE 11

Effect of compositions of present invention on body weight and muscle mass

| Sr. No. | Example | Dose per day (gms) | Initial Body weight (Kgs) | Body weight (after two months) in Kgs | Muscle mass increase in % over three months |
|---|---|---|---|---|---|
| 1 | 10% GOD + 25% Inulin + 50% beta glucan + 5% Mannitol + 10% Tagatose, as per an embodiment of the present invention | 25 | 60 | 55.8 | 6 |
| 2 | 6% GOD + 65% Beta glucan + 14% mannitol + 15% erythritol as per an embodiment of present the invention | 25 | 60 | 55.2 | 6 |
| 3 | 2% GOD + 1% Inulin + 1% Betaglucan + 96% Tagatose as per an embodiment of the present invention | 25 | 60 | 55.4 | 6.5 |
| 4 | 0.5% GOD + 2% Inulin + 94% Sucrose as per an embodiment of the invention | 25 | 60 | 54.8 | 6 |
| 5 | 6% GOD + 10% Inulin + 15% Beta glucan + 25% mannitol + 20% Erythritol + 24% Sucrose as per an embodiment of the invention | 25 | 60 | 54.2 | 6 |
| 6 | Sugar | 25 | 60 | 62.5 | No change |
| 7 | Splenda (Sucralose + Maltodextrin 95% + Dextrose) | 25 | 60 | 63.5 | No change |
| 8 | Acesulfame K containing artificial sweetener with 6% chitosan, sucrose and sorbitol as per US '439 | 25 | 60 | 63 | No change |
| 9 | Stevia (natural sugar substitute) containing sweetener with 6% chitosan, sucrose and sorbitol as per US '439 | 25 | 60 | 63.0 | No change |

TABLE 11-continued

Effect of compositions of present invention on body weight and muscle mass

| Sr. No. | Example | Dose per day (gms) | Initial Body weight (Kgs) | Body weight (after two months) in Kgs | Muscle mass increase in % over three months |
|---|---|---|---|---|---|
| 10 | 8% Chitosan + Sucrose + (xylitol) as per US '439 | 25 | 60 | 62 | No change |
| 11 | Control | — | 60 | 60.5 | No change |

It was surprisingly observed that an individual consuming the sweetener or the nutraceutical composition including 10% GOD+25% Inulin+50% beta glucan+5% Mannitol+10% Tagatose, 6% GOD+65% Beta glucan+14% mannitol+15% erythritol; 2% GOD+1% Inulin+1% Betaglucan+96% tagatose; 0.5% GOD+2% Inulin+94% Sucrose and 6% GOD+10% Inulin+15% Beta glucan+25% mannitol+20% Erythritol+24% Sucrose, as per the embodiments of the present invention showed a 5%-9.6% reduction in body weight rendering these compositions highly effective in controlling the body weight in diet conscious individuals. More interestingly, there was a substantial reduction in body fat which is evident from losing waist size from 1.0 inch to 3.25 inches without dieting and exercise. Moreover, the muscle mass was also found to be increased with the consumption of the sweetener composition as per the embodiment of the present invention, which is an encouraging factor.

It was further observed from the above table that the body weight increased with the consumption of sugar or with compositions containing artificial sweeteners such as sucralose or Acesulfame K. Further even the consumption of Stevia (natural sugar substitute) based composition also showed an increase of 3.5 kgs in the body weight of an individual consuming the same for a period of three months.

It was also seen that even the consumption of low intensity sweetener compositions such as xylitol led to an increase in the body weight of individuals consuming the same.

Thus, it can be observed that the sweetener or the nutraceutical compositions containing the glucose oxidase enzyme as per the embodiment of the present invention helps in maintaining the body weight of an individual as compared to sugar or other known sweeteners.

Example 11

Known sweetener compositions based on artificial sweeteners such as sucralose or Acesulfame K along with natural sugar substitute compositions including *stevia*, sugar, glucose and sucrose, were compared with the sweetener or the nutraceutical compositions containing glucose oxidase enzyme for their calorific values. The calorific values are determined using Bomb calorimeter. The results observed were tabulated as follows:

TABLE 12

Calories per 100 g of glucose oxidase compositions and sweetener compositions of present invention and sugars and other reported/marketed compositions

| Sr. No. | Product | Calories/100 g |
|---|---|---|
| 1 | 4% Glucose oxidase enzyme and 96% Beta glucan as per an embodiment of the invention | 300 |
| 2 | 4% GOD + 15% Inulin + 81% Mannitol as per an embodiment of the invention | 155 |
| 3 | 0.5% GOD + 2% Inulin + 94% Sucrose as per an embodiment of the invention | 340 |
| 4 | Sugar | 400 |
| 5 | Glucose | 400 |
| 6 | 8% Chitosan + Sucrose + (xylitol) as per US '439 | 400 |
| 7 | Splenda (Sucralose + Maltodextrin 95% + Dextrose) | 400 |
| 8 | Acesulfame K containing artificial sweetener with 6% chitosan, sucrose and sorbitol as per US '439 | 400 |
| 9 | Stevia (natural sugar substitute) containing sweetener with 6% chitosan, sucrose and sorbitol as per US '439 | 400 |
| 10 | Control | 400 |

It can be seen from the above table that the sweetener or the nutraceutical compositions 1-3 containing the glucose oxidase enzyme as per the embodiments of the present invention are beneficial in terms of reducing the daily calories consumed by an individual, as compared to other artificial sweetener compositions based on Sucralose or Acesulfame K or even other natural sugar substitute based sweetener compositions including *Stevia* or with consumption of glucose or table sugar, indicating that the compositions as per the embodiment of the present invention are highly suitable for diet conscious individuals.

Example 12: Compositions Containing Glucose Oxidase Enzyme (GOD), Dietary Fibres (Inulin or Beta Glucan) and Polyols or Sugar Alcohols (Mannitol or Erythritol)

TABLE 13

| | Sweetener composition | | | | | | |
|---|---|---|---|---|---|---|---|
| Ingredients | I (wt %) | II (wt %) | III (wt %) | IV (wt %) | V (wt %) | VI (wt %) | VII (wt %) |
| Glucose Oxidase Enzyme | 0.5 | 4 | 6 | 10 | 20 | 60 | 80 |
| Inulin | 45 | 70 | — | — | 25 | — | 10 |
| Beta glucan | 20 | — | 65 | 65 | 25 | 20 | — |
| Mannitol | 31 | 26 | 14 | — | 15 | — | 10 |
| Erythritol | 3.5 | — | 15 | 25 | 15 | 20 | — |

Process:
1. The glucose oxidase enzyme, Inulin and Beta glucan are thoroughly mixed to get a uniform blend.
2. To the blended mixture mannitol and erythritol are added and uniformly mixed to get the desired composition.

Example 13

Comparison of food article such as pudding containing i. sweetener composition with Glucose oxidase enzyme as per the embodiments of the present invention; ii Artificial sweetener (sucralose) based compositions iii. Natural sugar substitute based compositions and iv. Compositions containing low intensity sweeteners such as xylitol in terms of calorific values and blood sugar levels. The results observed were tabulated as follows:

It is surprisingly observed from the above table that individuals consuming Pudding containing sweetener compositions including Glucose oxidase enzyme (GOD) as per the embodiments of the present invention showed a good control in the blood sugar levels as well as effective weight control over a three months period. Instead subjects who were consuming Pudding with artificial sweetener compositions including sucralose or natural sugar substitutes such as *stevia* or those including low intensity sweeteners such as xylitol showed a steep increase in their blood sugar levels as well as an increase in their body weights. It can be seen that Pudding with known sweeteners exhibited poor glycemic control which was evident from elevating levels of blood sugar during the period of study whereas consuming bread with sweetener composition including GOD helps to manage weight effectively over known sweeteners which also induce flatulence and heaviness.

TABLE 14

Effect of food compositions of present invention on body weight and blood sugar levels of borderline cases

| Sr. No | Example | Intake per day | Initial Body weight (Kgs) | Body weight after 3 months (Kgs) | Blood sugar level before intake (mg/dl) | Blood sugar level one month after intake (mg/dl) |
|---|---|---|---|---|---|---|
| 1. | Pudding containing sweetener with 4% Glucose oxidase enzyme and 96% Beta glucan as per an embodiment of the invention | 2 pieces | 60 | 55.2 | 104 | 84 |
| 2. | Pudding containing sweetener with 0.5% GOD + 2% Inulin + 94% Sucrose as per an embodiment of the invention | 2 pieces | 60 | 56.3 | 101 | 87 |
| 3. | Pudding containing sweetener with 20% GOD + 10% Mannitol + 10% Erythritol + 50% Sorbitol + 10% xylitol as per an embodiment of the invention | 2 pieces | 60 | 55.9 | 108 | 89 |
| 4. | Pudding containing sweetener with 4% GOD + 70% Inulin + 26% mannitol as per an embodiment of the invention | 2 pieces | 60 | 55.2 | 106 | 91 |
| 5. | Pudding containing Splenda (Sucralose + Maltodextrin 95% + Dextrose) | 2 pieces | 60 | 64 | 103 | 123 |
| 6. | Pudding containing Stevia (natural sugar substitute) containing sweetener with 6% chitosan, sucrose and sorbitol as per US '439 | 2 pieces | 60 | 66 | 105 | 130 |
| 7. | Pudding containing 8% Chitosan + Sucrose + (xylitol) as per US '439 | 2 pieces | 60 | 64.5 | 101 | 118 |
| 8. | Control - Normal Pudding with chemical additives | 2 pieces | 60 | 62 | 99 | 108 |

Example 14

Six diabetic type 2 patients were randomly administered known sweeteners such as Sucralose and *Stevia* along with the sweetener or the nutraceutical composition containing glucose oxidase enzyme, as per the present invention, for their effect on the blood sugar concentration levels.

One patient was not given any composition. Before the onset of the study (week 0) and after 2 months, weight measurements were taken. The results observed were tabulated as follows:

Blood sugar values are compared for the same two subjects who were administered with these compositions:

TABLE 15

Sweetener composition effect on blood sugar levels

| Sr. No. | Example | Dose per day | Blood sugar level before administration (mg/dl) | Blood sugar level 2 hrs after administration (mg/dl) |
|---|---|---|---|---|
| 1 | 10% GOD + 25% Inulin + 50% Beta glucan + 5% mannitol + 10% Sucrose containing sweetener composition as per an embodiment of the invention | 25 gms | 99 105 | 85 97 |
| 2 | 4% Glucose oxidase enzyme + 15% Beta glucan + 41% sucrose + 40% tagatose as per an embodiment of the invention | 25 gms | 99 105 | 89 101 |
| 3 | Dextrose monohydrate | 25 gms | 96 105 | 156 170 |
| 4 | Stevia (natural sugar substitute) | 25 gms | 90 104 | 135 140 |
| 5 | Splenda (Sucralose + Maltodextrin 95% + Dextrose) containing sweetener with 6% chitosan, sucrose and sorbitol as per US '439 | 25 gms | 98 105 | 147 158 |
| 6 | Control | — | 104 | 139 |

It was observed from the above table that a steep increase in the blood sugar levels was observed in subjects administered with dextrose monohydrate as well as with *stevia* or sucrolose based sweeteners. It was surprisingly observed that the blood sugar is efficiently controlled with the sweetener or the nutraceutical compositions 1 and 2, containing the glucose oxidase enzyme as per the embodiment of the present invention.

Example 15

The pharmaceutical or nutraceutical composition containing glucose oxidase enzyme as per the present invention, Sucralose or *stevia* based sweetener composition and known sweeteners and antidiabetic drugs based on sulphonylureas and biguanides were given to 3 diabetic patients (Hyperglycemics & Hyperlipidaemic patients) with an advice to replace it totally for Sugar and their blood sugar levels were monitored for a period of 6 months.

Blood sugar levels Initial (Pre-trial) V/S lowering of blood sugar levels observed in 3 and 6 months are as tabulated in the table below:

TABLE 16

Sweetener composition effect on blood sugar levels

Patients were on antidiabetic medicine at least 3 months before the test and during the test

| Sr. No | Composition | Dosage (gms) | INITIAL Fasting | INITIAL PP | After 1 month Fasting | After 1 month PP | 3 Months Fasting | 3 Months PP | 6 months Fasting | 6 months PP |
|---|---|---|---|---|---|---|---|---|---|---|
| 1. | 10% GOD + 50% beta glucan + 40% tagatose based composition as per an embodiment of the invention | 25 | 140 | 187 | 130 | 147 | 126 | 130 | 115 | 125 |
| 2. | 4% Glucose oxidase enzyme + 15% Beta glucan + 41% sucrose + 40% tagatose as per an embodiment of the invention | 25 | 170 | 207 | 160 | 167 | 146 | 140 | 125 | 115 |
| 3. | 20% GOD + 20% Erythritol + 40% Sucrose + 20% Tagatose as per the embodiment of the invention | 25 | 215 | 250 | 160 | 148 | 147 | 132 | 90 | 105 |

TABLE 16-continued

Sweetener composition effect on blood sugar levels

Patients were on antidiabetic medicine at least 3 months before the test and during the test

| Sr. No | Composition | Dosage (gms) | INITIAL Fasting | PP | After 1 month Fasting | PP | 3 Months Fasting | PP | 6 months Fasting | PP |
|---|---|---|---|---|---|---|---|---|---|---|
| 4. | Stevia (natural sugar substitute) containing sweetener with 6% chitosan, sucrose and sorbitol as per US '439 | 25 | 145 | 185 | 160 | 210 | 165 | 215 | 160 | 210 |
| 5. | Splenda (Sucralose + Maltodextrin 95% + Dextrose) | 25 | 160 | 200 | 170 | 215 | 165 | 215 | 175 | 200 |
| 6. | Sulphonylurea based antidiabetic drug | 0.005 | 175 | 220 | 170 | 200 | 165 | 210 | 150 | 190 |
| 7. | Biguanides based antidiabetic drug | 0.005 | 180 | 230 | 175 | 215 | 160 | 212 | 158 | 210 |
| 8. | Control | N.A. | 190 | 225 | 195 | 225 | 190 | 222 | 192 | 220 |

From the above results, it is surprising to observe that the pharmaceutical or nutraceutical compositions 1-3 containing glucose oxidase enzyme as per the embodiments of the present invention showed excellent glycemic control in Hyperglycemic patients as compared to treatment with known nutraceutical compositions containing sucralose or stevia based sweeteners as well as in comparison with conventional antidiabetic drugs based on sulphonylureas and biguanides.

Example 16

Known pharmaceutical/nutraceutical compositions as well as other artificial sweeteners were compared to the pharmaceutical composition including the glucose oxidase enzyme of the invention for controlling oxidative stress in diabetic individuals.

Micronucleus is a small nucleus (also known as erratic or third nucleus), present in the cytoplasm of the cell. Formation of micronuclei indicates oxidative stress and genetic damage. The micronucleus assay using scraped buccal epithelial cells is an easy and non-invasive assay to estimate oxidative stress.

The results of the Non Invasive Micronucleus Assay, using buccal epithelial cells were tabulated as follows:

TABLE 17

Effect of Sweetener compositions upon oxidative stress

| Sr. No. | Composition | Dose (gms) | Oxidative stress Values (% of cells containing micronuclei) | |
|---|---|---|---|---|
| | | | before administration | one month after administration |
| 1 | Sugar | 40 | 5.0 | 7 |
| 2 | 6% GOD + 15% Mannitol + 45% Sucrose + 34% Tagatose based composition as per an embodiment of the invention | 40 Lowest effective dosage is 25 g | 5.0 | 3.2 3.35 |
| 3 | 2% GOD + 2% erythritol + 96% tagatose based composition as per an embodiment of the invention | 40 Lowest effective dosage is 25 g | 5.0 | 3.4 3.43 |
| 4 | Stevia (natural sugar substitute) containing sweetener with 6% chitosan, sucrose and sorbitol as per US '439 | 40 | 5.0 | 5.8 |
| 5 | Splenda (Sucralose + Maltodextrin 95% + Dextrose) | 40 | 5.0 | 8 |
| 6 | Sulphonylurea containing antidiabetic drug | 0.005 | 5.0 | 4.7 |
| 7 | Antioxidant drug such as Cordyceps | 0.005 | 5.0 | 4.4 |
| 8 | Control | — | 5.0 | 5.2 |

It is observed from the above table that there is a surprisingly high reduction in the oxidative stress values after with the administration of the nutraceutical or the pharmaceutical composition comprising the glucose oxidase enzyme (compositions 1 and 2) as per the embodiment of the pending application as compared to the reduction observed with the conventional antidiabetic drugs. In fact, it was observed that there is an increase in the oxidative stress values with the consumption of artificial sweeteners compositions including stevia or sucralose or with the consumption of sugar.

Example 17

The HbA1c Values of diabetic individuals were monitored after administration of known diabetic drugs (sulphonyl urea or Biguanides), with the administration of insulin, and with the administration of a pharmaceutical or nutraceutical compositions containing glucose oxidase enzyme, as per the embodiment of the present invention. Comparisons were also made with Sucralose or *stevia* based sweetener composition and other known sweeteners. The observations are set forth in the table below. The HbA1c Values of these diabetic individuals were monitored over a period of 3 months, 6 months and 12 months respectively. HbA1c is a lab test that measures the number of glucose molecules attached to haemoglobin, whereby the test gives a better average of blood sugar management with diabetics since it is averaged over 2-3 months, in contrast to the daily high/low glucose fluctuations when measuring blood sugar.

The observations are set forth in the table below individuals consuming artificial sweeteners based on *stevia* after 12 months of their consumption. It can be further seen from the above table that there is only a slight reduction of as low as 1-2% in the HbA1C values in patients administered with Sulphonylurea based antidiabetic drugs and Thiazolidinediones based antidiabetic drugs.

Surprisingly, there has been a substantial reduction of over 30% in the HbA1c Values after administration of the Glucose oxidase enzyme containing pharmaceutical or nutraceutical composition, as per the embodiment of the pending application.

TABLE 18

Effect of further compositions on glycated haemoglobin levels

| Sr. No | Composition | Patient | Dose per day (gms) | INITIAL HbA1C | 3 Months HbA1C | 6 Months HbA1C | 12 Months HbA1C |
|---|---|---|---|---|---|---|---|
| 1 | 8% Glucose oxidase enzyme + 35% Inulin 10% Beta glucan + 10% sucrose + 37% tagatose as per an embodiment of the invention | Patient 1 | 40 | 12 | 10.7 | 9.4 | 8 |
| | | Patient 2 | 40 | 8.9 | 7.5 | 6.8 | 6.2 |
| | | Patient 3 | 40 | 10.12 | 9 | 7.82 | 6.92 |
| 2 | 10% Glucose oxidase enzyme + 50% Beta glucan + 40% sucrose as per an embodiment of the invention | Patient 1 | 40 | 12 | 10.5 | 9.5 | 8.3 |
| | | Patient 2 | 40 | 8.9 | 7.7 | 7.1 | 6.5 |
| | | Patient 3 | 40 | 10.12 | 9.2 | 7.9 | 7.2 |
| 3 | Stevia (natural sugar substitute) containing sweetener with 6% chitosan, sucrose and sorbitol as per US '439 | Patient 1 | 40 | 12 | 12.4 | 12.2 | 12.3 |
| | | Patient 2 | 40 | 8.9 | 8.92 | 8.9 | 8.95 |
| | | Patient 3 | 40 | 10.12 | 10.15 | 10.14 | 10.12 |
| 4 | Sulphonylurea based antidiabetic drug | Patient 1 | 0.005 | 12 | 11.91 | 11.88 | 11.85 |
| | | Patient 2 | 0.005 | 10 | 9.925 | 9.90 | 9.60 |
| | | Patient 3 | 0.005 | 8 | 7.92 | 7.90 | 7.86 |
| 5 | Thiazolidinediones based antidiabetic drug | Patient 1 | 0.005 | 12 | 11.88 | 11.85 | 11.78 |
| | | Patient 2 | 0.005 | 10.12 | 10.01 | 9.98 | 9.94 |
| | | Patient 3 | 0.005 | 8.90 | 8.81 | 8.77 | 8.72 |
| 6 | Control | Patient 1 | N.A. | 12 | 12 | 12 | 12 |
| | | Patient 2 | N.A. | 8.9 | 8.9 | 8.9 | 8.9 |
| | | Patient 3 | N.A. | 10.12 | 10.12 | 10.12 | 10.12 |

It is observed from the above table that there is a substantial reduction in the HbA1C values over a period of 12 months which is observed in diabetic patients with the administration of the pharmaceutical or the nutraceutical composition comprising 8% Glucose oxidase enzyme+35% Inulin 10% Beta glucan+10% sucrose+37% tagatose as per an embodiment of the invention as well as the composition 10% Glucose oxidase enzyme+50% Beta glucan+40% sucrose as per an embodiment of the invention, both of which are prepared as per the embodiments of the pending application. In fact, it can be observed from the above table that there has been an increase in the HbA1C Values in Example 18

Observations in the blood triglyceride levels and cholesterol levels of diabetic individuals were made after the consumption of the pharmaceutical or nutraceutical composition containing glucose oxidase enzyme, as per the embodiment of the present invention and in comparison to known artificial sweeteners such as sucralose or sweeteners based on natural sugar substitute such as *stevia*. The observations are set forth in the table below:

TABLE 19

Effect of further compositions on triglycerides and cholesterol levels

| Sr. No | Composition details | Dose (gms) | Triglyceride levels Before administration (mg/dL) | Triglyceride levels three months after administration (mg/dL) | Cholesterol levels before administration (mg/dL) | Cholesterol levels three months after administration (mg/dL) |
|---|---|---|---|---|---|---|
| 1 | 2% GOD + 4% Inulin + 4% Beta glucan + 5% Mannitol + 5% Erythritol + 50% Sucrose + 30% Tagatose based nutraceutical or pharmaceutical composition as per an embodiment of the invention | 40 | 220 | 161 | 260 | 182 |
| 2 | 10% GOD + 25% Inulin + 50% Beta glucan + 5% Mannitol + 10% Sucrose based nutraceutical or pharmaceutical composition as per an embodiment of the invention | 40 | 225 | 162 | 262 | 186 |
| 3 | Stevia (natural sugar substitute) containing sweetener with 6% chitosan, sucrose and sorbitol as per US '439 | 40 | 210 | 235 | 250 | 275 |
| 4 | Splenda (Sucralose + Maltodextrin 95% + Dextrose) | 40 | 230 | 240 | 245 | 268 |
| 5 | 8% Chitosan + Sucrose + (xylitol) as per US '439 | 40 | 230 | 245 | 235 | 255 |
| 6 | Control | — | 210 | 215 | 240 | 248 |

Conclusions: It is observed that the triglyceride levels are effectively controlled with the nutraceutical or pharmaceutical compositions 1 and 2 containing 2% GOD+4% Inulin+4% Beta glucan+5% Mannitol+5% Erythritol+50% Sucrose+30% Tagatose as well as 10% GOD+25% Inulin+50% Beta glucan+5% Mannitol+10% Sucrose based compositions, respectively, prepared as per the embodiments of the invention, as compared to consumption of known artificial sweetener compositions 3-5, which are based on Stevia or sucralose or compositions containing low intensity sweeteners such as xylitol. It was further observed that cholesterol levels are efficiently controlled with the compositions 1 and 2 as per the embodiments of the invention as compared to compositions 3-5 with known sweeteners. In fact, there is a reduction of around 30% in the triglyceride levels and the cholesterol levels with the consumption of glucose oxidase enzyme based compositions as compared to consumption of known sweeteners. As illustrated above, the compositions containing the glucose oxidase enzyme as per the embodiments of the present invention can be used in humans to eliminate their dependence on diabetic drugs and thereby obviate the side effects shown by such drugs.

Example 19

Observations in the blood sugar levels and body weight of diabetic individuals were made after the consumption of the pharmaceutical or nutraceutical composition containing glucose oxidase enzyme, as per the embodiment of the present invention and in comparison, to known artificial sweeteners such as sucralose or sweeteners based on natural sugar substitute such as *stevia*. Compositions 1-4 containing Glucose Oxidase Enzyme administered to patients with Hyperglycemia for the period up to 90 days. Their body weights were also monitored.

The observations are set forth in the table below:

TABLE 20

Effect of further compositions on blood sugar and body weight

| | | | Consumption of compositions A/B/C/D | | | | |
|---|---|---|---|---|---|---|---|
| | | | Blood Sugar | | | Body Weight | |
| Sr. No | Composition Details | Dose (gms) | Day 0 (At least for 3 months on antidiabetic medicine) | 30 days | 90 days | 0 days | 90 days |
| 1 | Composition A GOD + 80% B-D Arabino Hexulose + 5% Inulin Prebiotic dietary fibre + 5% Beta Glucan + 7% Xylitol | 25 | 178 129 267 156 | 145 105 200 148 | 128 95 176 130 | 76 89 90 76 | 71 83 83 72 |
| 2 | Composition B 5% GOD + 35% B-D Arabino Hexulose + 10% Inulin Prebiotic dietary fibre + 10% Beta Glucan + 30% Xylitol + 10% Erythritol | 25 | 256 109 267 156 | 225 105 210 148 | 145 95 160 130 | 76 89 83 67 | 73 85 78 65 |
| 3 | Composition C 4% GOD + 35% B-D Arabino Hexulose + 15% Beta Glucan + 10% Mannitol + 10% Tagatose + 20% Erythritol + 6% Sucrose + 5% Bilberry Costus Igneus Extract | 25 | 160 270 109 267 | 150 170 103 167 | 130 135 95 119 | 80 104 68 75 | 74 95 61 70 |
| 4 | Composition D 10% GOD + 40% Inulin Prebiotic dietary fibre + 25% Beta Glucan + 5% Cranberry Extract + 5% Bilberry Costus Igneus Extract + 15% Galactomannan | 25 | 167 190 270 109 | 150 145 170 103 | 120 125 135 95 | 87 94 90 60 | 80 88 82 55 |

Conclusion:

It is observed that the blood sugar levels and body weight are effectively controlled with the further compositions 1 to 4 wherein, prepared as per the embodiments of the invention as compared to consumption of known artificial sweetener sucralose (refer table 15, composition 5), and also sweetener compositions which are based on *Stevia* (refer table 15, composition 4).

Compositions A to D prepared in accordance with the present invention lead to 6-8% weight loss in 3 months without any adverse side effects observed.

Example 20

Observations of glucose tolerance test on healthy volunteers were made after the consumption of the sweetener composition containing glucose oxidase enzyme, as per the embodiment of the present invention and in comparison, to known artificial sweetener product having artificial sweetener sucralose and bulking agent dextrose monohydrate.

The observations are set forth in the table below:

TABLE 21

Glucose tolerance test applied to sweetener composition

| Sr. No | Composition Details | Dose (gms) | Blood Sugar | |
|---|---|---|---|---|
| | | | Initial | After 2 hrs |
| 1 | Sweetener Composition of the present invention | 75 gms in 200 ml of water is offered to drink | 85 79 90 99 103 105 102 104 100 87 95 105 101 109 110 | 91 83 84 85 94 109 119 115 95 98 100 114 93 93 91 |

TABLE 21-continued

Glucose tolerance test applied to sweetener composition

| Sr. No | Composition Details | Dose (gms) | Blood Sugar Initial | Blood Sugar After 2 hrs |
|---|---|---|---|---|
| | | | 88 | 92 |
| | | | 91 | 91 |
| | | | 75 | 80 |
| | | | 73 | 83 |
| | | | 101 | 92 |
| | | | 76 | 80 |
| | | | Average/20 respondents- 98.9 | Average/20 respondents- 99.1 |
| 2 | Dextrose monohydrate | 75 gms in 200 ml of water is offered to drink | 80 | 141 |
| | | | 79 | 149 |
| | | | 97 | 160 |
| | | | 96 | 156 |
| | | | 100 | 160 |
| | | | 105 | 170 |
| | | | 104 | 175 |
| | | | 86 | 150 |
| | | | 89 | 145 |
| | | | 98 | 149 |
| | | | 105 | 158 |
| | | | 102 | 169 |
| | | | 104 | 154 |
| | | | 100 | 159 |
| | | | 87 | 149 |
| | | | 95 | 156 |
| | | | 99 | 157 |
| | | | 102 | 164 |
| | | | 103 | 161 |
| | | | 93 | 160 |
| | | | Average/20 respondents- 92.2 | Average/20 respondents- 157.1 |
| 3 | Sugar substitute (sucralose based) | 75 gms in 200 ml water is offered to drink | 78 | 140 |
| | | | 75 | 148 |
| | | | 87 | 156 |
| | | | 90 | 165 |
| | | | 96 | 160 |
| | | | 98 | 164 |
| | | | 98 | 157 |
| | | | 86 | 150 |
| | | | 89 | 149 |
| | | | 93 | 159 |
| | | | 105 | 168 |
| | | | 102 | 149 |
| | | | 104 | 154 |
| | | | 76 | 139 |
| | | | 80 | 149 |
| | | | 99 | 156 |
| | | | 87 | 147 |
| | | | 100 | 164 |
| | | | 105 | 161 |
| | | | 97 | 150 |
| | | | Average/20 respondents- 92.25 | Average/20 respondents- 154.25 |

Conclusion:

The Glycemic Response of sweetener composition of the present invention is found to be best suitable for Diabetics. Artificial sweetener, sucralose respond almost in the same manner as that of Glucose. Most of the artificial sweeteners use Glucose/Dextrose monohydrate as the bulking agent which has glycemic index of 100 or more.

TABLE 22

Anti- diabetic preparation comprising Glucose oxidase composition

| Ingredients | Ingredients | Ingredients | Ingredients | Quantity in mg |
|---|---|---|---|---|
| Metformin | Metformin | Metformin | Metformin | 500-1000 |
| Povidone K-30 | Povidone K-30 | Povidone K-30 | Povidone K-30 | 25-50 |
| Starch | Starch | Starch | Starch | 50-100 |
| Magnesium stearate | Magnesium stearate | Magnesium stearate | Magnesium stearate | 5-10 |
| Maltodextrin | Maltodextrin | Maltodextrin | Maltodextrin | 25-50 |
| Glucose oxidase | Glucose oxidase | Glucose oxidase | Glucose oxidase | 10-20 |
| Inulin | Pectin | Beta galactomannan | Beta glucan | 20-40 |

Process

1. Blend glucose oxidase and dietary fibre
2. Blend metformin, starch and blend of step 1
3. Prepare binder solution of Povidone K-30 in water
4. Granulate the blend of step 2 with binder solution of step 3
5. Mill the granulate of step 4
6. Dry the granulate
7. Mill the dried granules
8. Blend the dried granules with maltodextrin and magnesium stearate
9. Compress the tablets at an average weight of 605 mg or 1210 mg.

TABLE 23

Anti- diabetic preparation comprising Glucose oxidase composition

| INGREDIENT (mg) | F1 | F2 | F3 |
|---|---|---|---|
| Gliclazide | 40 | 40 | 40 |
| Lactose (Diluent) | 173.75 | 171.25 | 168.75 |
| Sodium Starch Glycolate (3-5%) | 7.5 | 10 | 12.5 |
| Talc (0.5%) | 1.25 | 1.25 | 1.25 |
| Magnesium stearate (1%) | 2.5 | 2.5 | 2.5 |
| Glucose oxidase enzyme (5%) | 12.5 | 12.5 | 12.5 |
| Inulin (5%) | 12.5 | — | — |
| Beta glucan (5%) | — | 12.5 | — |
| Pectin (5%) | — | — | 12.5 |
| Total weight | 250 | 250 | 250 |

Process

1. The tablets were prepared by geometrically mixing the ingredients and compressed using direct compression method.

2. The Gliclazide, Lactose, glucose oxidase enzyme, inulin, beta glucan, pectin and Sodium Starch Glycolate are thoroughly mixed and the magnesium stearate and Talc are added and mixed before the compression process.

TABLE 24

Biscuit preparation comprising Glucose oxidase composition

| INGREDIENT | Quantity |
|---|---|
| Plain flour | 175 g |
| Glucose oxidase enzyme | 10 g |
| Inulin | 15 g |
| Caster sugar | 50 g |
| Butter | 100 g |
| Vanilla extract | q.s |
| Total | 350 g |

Process:
1. Preheat the oven to 150° C.
2. Add butter and sugar in a bowl and mix well until light and fluffy.
3. Add the vanilla, mix, then add the flour, Inulin, glucose oxidase enzyme and mix well.
4. Roll out to about 5 mm. Cut into shapes.
5. Bake for 25 minutes or until golden brown.

The sweetener, nutraceutical and the pharmaceutical compositions containing glucose oxidase enzyme as per the embodiments of the present invention appear to alleviate the effects of known antidiabetic drugs in lowering the blood sugar concentrations. It is observed that when composition of the invention is ingested or administered it co-acts with the insulin normally present in the body to reduce blood sugar concentrations by direct oxidation of glucose or by increasing the speed of the entire metabolic carbohydrate degradation process and by maintaining the insulin in its R—S—S—R active cysteinic form as opposed to the R—SH cysteine form which is inactive.

Although the invention has been described in detail for the purpose of illustration, it is understood that such detail is solely for that purpose and variations can be made therein by those skilled in the art without departing from the spirit and scope of the invention which is defined by the following claims.

From the foregoing, it will be observed that numerous modifications and variations can be effectuated without departing from the true spirit and scope of the novel concepts of the present invention. It is to be understood that no limitation with respect to the specific embodiments illustrated is intended or should be inferred.

TABLE 25

Nutraceutical composition

| Sr. No | Ingredients | Sample A (wt %) | Sample B (wt %) | Sample C (wt %) | Sample D (wt %) |
|---|---|---|---|---|---|
| 1. | Glucose oxidase enzyme | 10 | 15 | 5 | 3 |
| 2. | Blue berry extract | — | 5 | — | — |
| 3. | Inulin | 35 | 35 | 5 | 5 |
| 4. | Beta glucan | 20 | 15 | 3 | 5 |
| 5. | Pectin | — | 5 | — | — |
| 6. | Pine bark extract | — | — | 1 | — |
| 7. | Branched chain amino acid Glutathione or N acetyl cysteine | 4 | — | — | — |
| 8. | Vitamins D3/B12/K2-7/Beta carotene | 1 | 2 | — | — |
| 9. | Minerals | 1 | 2 | — | — |
| 10. | Calcium orotate/ Iron/Magnesium | | | | |
| 11. | *Costus igneus* (Insulin Plant) extract | 4 | 10 | — | 1 |
| 12. | Galactomanan | 15 | 10 | — | — |
| 13. | Resveratrol (Grape seed extract) | — | — | — | 1 |
| 14. | Cranberry extract | — | — | 1 | — |
| 15. | B-D Fructose | — | — | 85 | 75 |
| 16. | Xylitol | — | — | 0 | 5 |
| 17. | Polydextrose | — | — | 3 | 5 |
| | Total | 100 | 100 | 100 | 100 |

We claim:

1. A glucose oxidase composition comprising glucose oxidase from 0.01-95% and at least one more ingredient comprising at least one low glycemic index nutritive ingredient with a glycemic index of less than 70 in an amount of at least 5%,
    wherein the said low glycemic index nutritive ingredient is selected from the group consisting of,
    (i) a dietary fibre;
    (ii) a saccharide;
    (iii) a polyol or a sugar alcohol, and
    wherein the said glucose oxidase composition produces a further composition selected from the group consisting of a food composition, a composition for fortification of food, a sweetener composition, a nutraceutical composition, and a pharmaceutical composition.

2. The glucose oxidase composition as in claim 1 wherein the said at least one polyol or a sugar alcohol is selected from one or more of mannitol, xylitol, maltitol, isomalt, inositol, erythritol, lactitol, glycerol (glycerine), sorbitol, arabitol, ribitol, polyglycetol, a hydrogenated starch hydrolysate (HSH), threitol, fruitol, iditol, volemitol, lactitol, galactitol, palatinose, palatinit, propylene glycol, a reduced isomalto-oligosaccharide, a fructooligosaccharide, a maltooligosaccharide, a reduced xylo-oligosaccharide, a reduced gentiooligosaccharide, reduced maltose syrup, reduced glucose syrup, reduced starch sugar, and combinations thereof.

3. The glucose oxidase composition as in claim 1, wherein said at least one saccharide is selected from one or more of fructose, tagatose, rhamnose, a dextrin, maltodextrin, dextran, ribulose, threose, arabinose, xylose, lyxose, allose, altrose, mannose, idose, levulose, maltose, invert sugar, isotrehalose, neotrehalose, palatinose or isomaltulose, erythrose, deoxyribose, gulose, idose, talose, erythrulose, xylulose, psicose, turanose, cellulose, cellobiose, starch, pectin, glucosamine, mannosamine, fucose, glucuronic acid, gluconic acid, glucono-lactone, glycogen, abequose, galactosamine, a beet oligosaccharide, an isomalto-oligosaccharide, a xylo-oligosaccharide, a gentio-oligosaccharide, sorbose, a nigero-oligosaccharide, a palatinose oligosaccharide, fucose, a fructo-oligosaccharide, maltotetraol, maltotriol, a malto-oligosaccharide, lactulose, melibiose, raffinose, rhamnose, ribose, an isomerized liquid sugar, a coupling sugar, a soybean oligosaccharide, and glucose syrup.

4. The glucose oxidase composition as in claim 1, wherein said dietary fibre is one or more of a non-starch polysaccharide, methylcellulose, a β-glucan, mucilage, a wax, a cyclodextrine, a cellulose, a hemicellulose, a starch, a dextrin, an inulin, a lignin, a chitin, a pectin, a beta-glucan, a fibre extracted from a legume, Chitosan, a natural gum, xanthan gum, guar gum, gellan gum, tara gum, gum acacia, gum arabic, beta-mannan, locust bean gum, psylium seed husk gum, galactomannan, glucomannan or konjac, karaya, tragacanth, a hexose, a pentose, resistant starch, a plant wax, an alginic acid (alginates), natriumalginat, kaliumalginat, ammoniumalginat, calciumalginat, propylenglycolalginat (PGA), agar, carrageen, raffinose, xylose, polydextrose, lactulose, a vegetable gum, polysaccharide, a heterosaccharide, agar-agar, alginate, an oligosaccharide, arabinoxylan, a fructooligosaccharide (FOS, oligofructose), a galacto-oligosaccharide (GOS), a human milk oligosaccharide (HMO), an isomalto-oligosaccharide (IMO), lactosucrose, a mannan-oligosaccharide (MOS), raffinose, stachyose, and verbascose.

5. The food composition, composition for fortification of food, sweetener composition, nutraceutical composition and pharmaceutical composition according to claim 1, further comprising at least one additional ingredient selected from the group consisting of a sweetening agent, a dietary fibre, a polysaccharide, a saccharide, a carbohydrate, a polyol, a sugar alcohol, a digestive enzyme, an antioxidant, a nucleotide, a nucleic acid, a vitamin, a mineral, an essential amino acid, a non-essential amino acid, a branched chain amino acid (BCAA), Leucine, Isoleucine, Valine, glutathione, Human growth hormone (HGH), N-acetyl cysteine, S Adenosyl, L-Methionine (SAMe), a plant extract, a fruit extract, insulin, a sulfonylurea, a biguanide, a gliptin, a pharmaceutically active ingredient, an anti-hypertensive, a medicine used for treatment of elevated total cholesterol, low density lipoproteins (LDL), and/or triglyceride, and a medicine used to elevate high-density lipoproteins (HDL).

6. The sweetener composition as in claim 5 comprising at least 0.01% of glucose oxidase, and at least 10% of one sweetening agent.

7. The sweetener composition as in claim 6 further comprising a dietary fibre.

8. The sweetener composition as in claim 7 comprising at least 0.01% of glucose oxidase, at least 0.1% dietary fibre and up to 99% of the sweetening agent.

9. The sweetener composition as in claim 7 comprising from 0.1-40% glucose oxidase, from 0.1%-89% dietary fibre and at least 10% of the sweetening agent.

10. The sweetener composition as in claim 7 comprising from 0.1-10% glucose oxidase, from 0.1%-70% dietary fibre and at least 10% of the sweetening agent.

11. The sweetener composition as in claim 7 comprising from 0.1-10% glucose oxidase, from 1%-30% dietary fibre and at least 10% of the sweetening agent.

12. The sweetener composition as in claim 6 wherein the sweetening agent is one or more of mannitol, xylitol, maltitol, isomalt, erythritol, lactitol, glycerol, sorbitol, polyglycetol, hydrogenated starch hydrolysates (HSH), fructose, galactose, sucrose, lactose, tagatose, high fructose corn syrup (HFCS)-42, HFCS-55, HFCS-90, caramel, golden syrup, inverted sugar, refiners syrup, maple syrup, honey, sorghum, syrup, cane juice, barley malt syrup, coconut palm sugar, brown rice syrup, and agave syrup.

13. A food or nutraceutical composition comprising the sweetener composition according to claim 6.

14. The nutraceutical composition as in claim 5, wherein the additional ingredient is or more of a dietary fibre, a digestive enzyme, an antioxidant, a nucleotide, a nucleic acid, a vitamin, a mineral, an essential amino acid, a non-essential amino acid, a branched chain amino acid (BCAA), a speciality neutraceutical selected from glutathione, Human growth hormone (HGH), S Adenosyl L-Methionine (SAMe), D-Ribose, N-acetyl cysteine, and a plant extract.

15. The nutraceutical composition as in claim 14 wherein said plant extract is one or more of pine bark extract, *Costus igneus* extract, bilberry extract, cranberry extract, blueberry extract, Gooseberry Extract, Rosemary Extract, *Gymnema sylvestra*, mangosteen extract, pineapple extract, and kiwi extract, and combinations thereof.

16. The nutraceutical composition as in claim 14 wherein said digestive enzyme is one or more of papain, bromelain, Lipase, amylase, glucoamylase, beta glucanase, Fructosyl Transferase and combinations thereof.

17. The food composition as in claim 5, wherein the dietary fibre is selected from the group consisting of a non-starch polysaccharide, methylcellulose, a β-glucan, mucilage, a wax, a cyclodextrin, a cellulose, a hemicelluloase, a starch, a dextrin, an inulin, a lignin, a chitin, a pectin, a beta-glucan, a fibre extracted from a legume, Chitosan, a natural gum, xanthan gum, guar gum, gellan gum, tara gum, gum acacia, gum arabic, beta-mannan, locust bean gum, psylium seed husk gum, galactomannan, glucomannan, konjac, karaya, tragacanth, a hexose, a pentose, a resistant starch, a plant wax, an alginic acid (alginate), natriumalginat, kaliumalginat, ammoniumalginat, calciumalginat, propylenglycolalginat (PGA), agar, carrageen, raffinose, xylose, polydextrose, lactulose, a vegetable gum, a polysaccharide, a heterosaccharide, agar-agar, alginate, an oligosaccharide, arabinoxylan, a fructooligosaccharide (FOS, oligofructose), a galacto-oligosaccharide (GOS), a human milk oligosaccharide (HMO), an isomalto-oligosaccharide (IMO), lactosucrose, a mannan-oligosaccharide (MOS), raffinose, stachyose, and verbascose.

18. The food composition as in claim 17 wherein the said food composition is in the form of a biscuit, a snack, a confectionary, a bakery product, a beverage, a juice, a product made from a fruit or a vegetable, a sauce, a jam, a jelly, already to eat food, a ready to cook food, a sweet, and/or a desert.

19. The pharmaceutical composition as in claim 5 comprising a pharmaceutically active ingredient, glucose oxidase and a dietary fibre.

20. The pharmaceutical composition as in claim 19, wherein the pharmaceutically active ingredient is one or more of anti-diabetics, anti-hypertensives, a medicine used for treatment of elevated total cholesterol, a medicine used for treatment of low density lipoprotein (LDL), triglycerides, a medicine used to elevate high density lipoprotein (HDL) cholesterol, a medicine for Alzheimer's symptoms, and a medicine for Parkinson's disease.

21. The pharmaceutical composition as in claim 19 wherein the dietary fibre is one or more of a non-starch polysaccharide, a methylcellulose, a β-glucan, mucilage, a wax, a cyclodextrin, a cellulose, a hemicellulose, a starch, a dextrin, an inulin, a lignin, a chitin, a pectin, a beta-glucan, a fibre extracted from a legume, Chitosan, a natural gum, xanthan gum, guar gum, gellan gum, tara gum, gum acacia, gum arabic, beta-mannan, locust bean gum, psylium seed husk gum, galactomannan, glucomannan, konjac, karaya, tragacanth, a hexose, a pentose, resistant starch, a plant wax, an alginic acid (alginate), natriumalginat, kaliumalginat, ammoniumalginat, calciumalginat, propylenglycolalginat (PGA), agar, carrageen, raffinose, xylose, polydextrose, lactulose, a vegetable gum, a polysaccharide, a heterosaccharide, agar-agar, alginate, an oligosaccharide, arabinoxylan, a fructooligosaccharide (FOS, oligofructose), a galacto-oligosaccharide (GOS), a human milk oligosaccharide (HMO), an isomalto-oligosaccharide (IMO), lactosucrose, a mannan-oligosaccharide (MOS), raffinose, stachyose, and verbascose.

22. The pharmaceutical composition of claim 19 wherein the composition is effective for controlling one or more of hyperglycemia, hypoglycemia, weight management challenges, obesity, oxidative stress, hyperuricemia, ketoacidosis, nonketotic hyperosmolar coma, cardiovascular disease, heart stroke, nephropathy, microalbuminuria, insulin resistance, amyloid foot ulcers, diabetic retinopathy, nonproliferative diabetic retinopathy, proliferative diabetic retinopathy, diabetic macular edema, cataract, glaucoma, High blood cholesterol (HDL) and low density lipoproteins (LDL), triglycerides, atherosclerosis, hypertension, metabolic disorders, constipation, inflammatory bowel disease, ulcerative colitis, Crohn's disease, diverticulitis, neuropathy, coeliac disease, hypothyroidism, hyperthyroidism, polycystic ovarian syndrome, diabetes insipidus, necrobiosis lipoidica diabeticorum, mastopathy, limited joint mobility, frozen shoulder, dupuytren's contracture, trigger finger, carpal tunnel syndrome, gingivitis, periodontitis, dental caries, xerostomia, oral thrush, cognitive dysfunction, Alzheimer's symptoms, and Parkinson's disease.

23. The food composition, composition for fortification of food, sweetener composition, nutraceutical composition and pharmaceutical composition according to claim 5 wherein said composition is in the form of a Powder composition, a granule composition, a crystalline composition, a pellet, a pill, a tablet, a hard or soft capsule composition, a powder for an oral suspension, an elixir, a gel, a sachet, a liquid solution, a suspension, or a sterile preparation.

24. The food composition, composition for fortification of food, sweetener composition, nutraceutical composition and pharmaceutical composition as in claim 23 in the form of a capsule.

25. The food composition, composition for fortification of food, sweetener composition, nutraceutical composition and pharmaceutical composition as in claim 23 in the form of a sachet.

26. A modified sugar comprising the sweetener composition according to claim 6.

27. The modified sugar of claim 26 comprising at least 50% of the sweetening agent.

28. The composition for fortification of food according to claim 5, wherein the additional ingredient is one or more of β-glucan, galactomannan, and inulin.

29. The composition for fortification of food according to claim 5, wherein the additional ingredient is one or more of a vitamin, a mineral, an amino acid, a fruit extract, an enzyme, an antioxidant, and a fibre.

30. The modified sugar of claim 26, wherein the sweetening agent is one or more of mannitol, xylitiol, maltitol, isomalt, erythritol, lactitol, glycerol, sorbitol, polyglycetol, a hydrogenated starch hydrolysate (HSH), fructose, galactose, sucrose, lactose, tagatose, high fructose corn syrup (HFCS)-42, HFCS-55, HFCS-90, caramel, golden syrup, inverted sugar, refiners syrup, maple syrup, honey, sorghum, syrup, cane juice, barley malt syrup, coconut palm sugar, brown rice syrup, and agave syrup.

* * * * *